United States Patent [19]
Tsujihara et al.

[11] Patent Number: 6,048,842
[45] Date of Patent: Apr. 11, 2000

[54] PROPIOPHENONE DERIVATIVES AND PROCESS FOR PREPARING THE SAME

[75] Inventors: Kenji Tsujihara, Urawa; Kunio Saito, Omiya; Mitsuya Hongu, Kawaguchi; Mamoru Matsumoto, Nara; Akira Oku, Toda, all of Japan

[73] Assignee: Tanabe Seiyaku Co., Ltd., Osaka, Japan

[21] Appl. No.: 08/993,523

[22] Filed: Dec. 18, 1997

[30] Foreign Application Priority Data

Dec. 26, 1996 [JP] Japan ................................. 8-347406

[51] Int. Cl.$^7$ ............................ A61K 31/70; C07H 15/00
[52] U.S. Cl. ........................................................... 514/25
[58] Field of Search .............................. 514/25; 536/4.1, 536/18.2, 18.3, 18.5, 18.1

[56] References Cited

U.S. PATENT DOCUMENTS

| | | |
|---|---|---|
| 3,984,394 | 10/1976 | Westall et al. . |
| 4,031,260 | 6/1977 | Westall et al. . |
| 4,665,058 | 5/1987 | Diedrich et al. . |
| 4,684,627 | 8/1987 | LeVeen et al. . |
| 4,760,135 | 7/1988 | Diedrich et al. . |
| 4,840,939 | 6/1989 | Leveen et al. . |
| 5,110,801 | 5/1992 | Leveen et al. . |

FOREIGN PATENT DOCUMENTS

| | | |
|---|---|---|
| 0598359A1 | 5/1994 | European Pat. Off. . |
| 0684254A1 | 11/1995 | European Pat. Off. . |
| 0773226A1 | 5/1997 | European Pat. Off. . |

OTHER PUBLICATIONS

Textbook of Diabetes, $2^{nd}$ Ed., vol. 2, chap. 83.8–83.13 (1997).
The New England Journal of Medicine, vol. 331, pp. 1118–1193 (1994).
The Journal of Pharmacology and Experimental Therapeutics, vol. 275, pp. 194–199 (1995).
Biochim Biophys. Acta, 71, 668, "The Comparative Effects of Some Phlorizin Analogs on the Renal Reabsorption of Glucose", pp. 688–700, 1963.
Diabetes Cares, vol. 13, No. 6, "Glucose Toxicity", pp. 610–630, 1990.
J. Clin. Invest., vol. 79, Correction of Hyperglycemia with Phlorizin Normalizes Tissue Sensitivity to Insulin in Diabetic Rats, pp. 1510–1515, 1987.
J. Clin. Invest., vol. 80, "Effect of Chronic Hyperglycemia on In Vivo Insulin Secretion in Partially Pancreatectomized Rats", pp. 1037–1044, 1987.
J. Clin. Invest., vol. 87, "Normalization of Blood Glucose in Diabetic Rats with Phlorizin Treatment Reverses Insulin-resistant Glucose Transport in Adipose Cells without Restoring Glucose Transporter Gene Expression", pp. 561–570, 1991.

Diabetologia, vol. 28, "Hyperglycaemia as an inducer as well as a consequence of impaired isle cell function and insulin resistance: implications for the management of diabetes", pp. 119–121, 1985.
Stroke, vol. 14, "Rapid, Transient Drop in Brain Glucose After Intravenous Phloretin or 3–0–Methyl–D–Glucose", pp. 388–393, 1983.
Biochemistry, vol. 8, No. 5, "The Inhibition of Photophosphorylation by Phlorizin and Closely Related Compounds", pp. 2067–2073, 1969.
American Journal of Physiology, vol. 224, No. 3, "Reevaluation of renal tubular glucose transport inhibition by phlorizin analogs", pp. 552–557, 1973.
Archives of Biochemistry and Biophysics, vol. 117, "Competitive Inhibition of Intestinal Glucose Transport by Phlorizin Analogs", pp. 248–256, 1966.
Archives of Biochemistry and Biophysics, vol. 199, No. 2, "The Affinity of Phlorizin–Like Compounds for a β–Glucosidase in Intestin Brush Borders: Comparison with Glucose Transport System", pp. 342–348, 1980.
Biochim. Biophys. Acta, 290, "Inhibition of [$^3$H] Phlorizin Binding to Isolated Kidney Brush Border Membranes by Phlorizin–Like Compounds", pp. 134–149, 1972.
J. Nutr. Sci. Vitaminol, 38 (1) pp. 27–37, ISSN 0301–4800, Tokyo, Japan, Feb. 1992.
Diabetes, vol. 37, "Characterization of New Oral Antidiabetic Agent CS–045", pp. 1549–1558, 1988.
Acta Alimentaria, vol. 11 (1), "Effect of a Synthetic Dihydrochalcone Sweetener (Chinoin–401) on Carbohydrate Metabolism", pp. 31–37, 1982.

*Primary Examiner*—Elli Peselev
*Attorney, Agent, or Firm*—Birch, Stewart, Kolasch & Birch, LLP

[57] ABSTRACT

A propiophenone derivative of the formula (I):

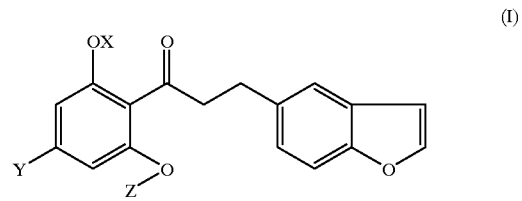

(I)

wherein OX is a hydroxy group which may optionally be protected, Y is a lower alkyl group, and Z is a β-D-glucopyranosyl group wherein one or more hydroxy groups may optionally be protected, or a pharmaceutically acceptable salt thereof. Said compounds have excellent hypoglycemic activity so that they are useful in the prophylaxis or treatment of diabetes.

24 Claims, No Drawings

PROPIOPHENONE DERIVATIVES AND PROCESS FOR PREPARING THE SAME

TECHNICAL FIELD

The present invention relates to a novel propiophenone derivative having a hypoglycemic activity, and a process for preparing the same.

PRIOR ART

Although diet therapy is essential in the treatment of diabetes, when diet therapy does not sufficiently control the conditions of patients, insulin or an oral antidiabetic is additionally used. There have been used as an antidiabetic biguanide compounds and sulfonylurea compounds. However, these antidiabetics have various side effects. For example, biguanide compounds cause lactic acidosis, and sulfonylurea compounds cause significant hypoglycemia. Under such circumstances, it has been desired to develop novel drugs for treatment of diabetes having no such side effects.

Recently, it has been reported that hyperglycemia participates in the outbreak and progressive impairment of diabetes, i.e., glucose toxicity theory. That is, chronic hyperglycemia leads to decrease insulin secretion and contributes to increase insulin resistance, and as a result, the blood glucose concentration is increased so that diabetes is self-exacerbated [cf. Diabetologia, Vol. 28, p. 119 (1985); Diabetes Care, Vol. 13, p. 610 (1990), etc.]. Therefore, by treating hyperglycemia, the aforementioned self-exacerbating cycle is interrupted so that the prophylaxis or treatment of diabetes is made possible.

As one of the methods for treating hyperglycemia, it is considered to excrete an excess amount of glucose directly into urine so that the blood glucose concentration is normalized.

Phlorizin is a glycoside which exists in barks and stems of Rosaceae (e.g., apple, pear, etc.). Recently, it has been found that phlorizin is an inhibitor of $Na^+$-glucose co-transporter which exists only in chorionic membrane of the intestine and the kidney, and by inhibiting $Na^+$-glucose co-transporter, phlorizin inhibits the renal tubular glucose reabsorption and promotes the excretion of glucose so that the glucose level in a plasma is controlled. Based on this action of phlorizin, when the glucose level in a plasma in diabetic animals is controlled at a normal level for a long time by subcutaneous daily administration of phlorizin, the conditions of diabetic animals are ameliorated to be normal [cf. Journal of Clinical Investigation, Vol. 79, p. 1510 (1987), ibid. Vol. 80, p. 1037 (1987), ibid. Vol. 87, p. 561 (1991), etc.].

However, when phlorizin is administered orally, most of it is hydrolyzed to afford glucose and phloretin, which is the aglycon of phlorizin, and hence, the amount of phlorizin to be absorbed is so little that the urine glucose excretion effect of phlorizin is very weak. Besides, phloretin, which is the aglycon of phlorizin, has been known to strongly inhibit a facilitated diffusion-type glucose transporter. For example, when phloretin is intravenously administered to rats, the glucose concentration in brain of rats is decreased [cf. Stroke, Vol. 14, p. 388 (1983)]. Therefore, when phlorizin is administered for a long time, there may be adverse effects on various tissues, and hence, phlorizin has not been used as an antidiabetic.

BRIEF DESCRIPTION OF INVENTION

An object of the present invention is to provide a 4'-lower alkylpropiophenone derivative which shows an urine glucose increasing activity because it inhibits the renal tubular glucose reabsorption, and shows an excellent hypoglycemic activity, and at the same time, whose aglycon has a very weak inhibitory activity of facilitated diffusion-type glucose transporter. Another object of the present invention is to provide a process for preparing a propiophenone derivative of the present invention. A further object of the present invention is to provide a hypoglycemic agent comprising as an active ingredient a propiophenone derivative of the present invention or a pharmaceutically acceptable salt thereof.

DETAILED DESCRIPTION OF INVENTION

The present invention relates to a propiophenone derivative of the formula (I):

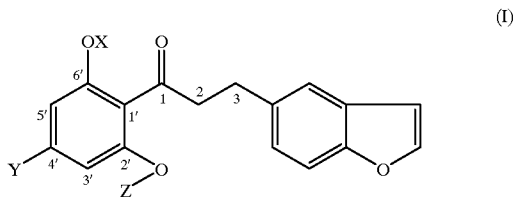

wherein OX is a hydroxy group which may optionally be protected, Y is a lower alkyl group, and Z is a β-D-glucopyranosyl group wherein one or more hydroxy groups may optionally be protected, or a pharmaceutically acceptable salt thereof.

Among the compounds (I) of the present invention, in case OX of the formula (I) is a protected hydroxy group, the protecting group may be any protecting group which can be a protecting group for a phenolic hydroxy group, for example, a lower alkoxy-lower alkyl group such as methoxymethyl group; an allyl group; and an acyl group such as a lower alkanoyl group, a lower alkoxy-lower alkanoyl group, a lower alkoxycarbonyl group, a lower alkoxy-lower alkoxycarbonyl group, an arylcarbonyl group (e.g., benzoyl group). Among these protecting groups, preferable ones are an acyl group such as a lower alkanoyl group, a lower alkoxy-lower alkanoyl group, a lower alkoxycarbonyl group, a lower alkoxy-lower alkoxycarbonyl group, and especially preferable ones are a lower alkanoyl group, and a lower alkoxycarbonyl group.

Among the compounds (I) of the present invention, in case Z of the formula (I) is a β-D-glucopyranosyl group wherein one or more hydroxy groups are protected, the protecting group may be any conventional protecting groups for hydroxy group which can easily be removed by a conventional method such as acid-treatment, hydrolysis, reduction, etc. The β-D-glucopyranosyl group wherein one or more hydroxy groups are protected by the above-mentioned protecting groups may be selected from (i) a β-D-glucopyranosyl group wherein one or more hydroxy groups are acylated, (ii) a β-D-glucopyranosyl group wherein two hydroxy groups combine to form a 1-lower alkoxy-lower alkylidenedioxy group, a benzylidenedioxy group, a phosphinicodioxy group, or a carbonyldioxy group together with the protecting groups thereof, and (iii) a β-D-glucopyranosyl group wherein one or two hydroxy groups are acylated, and the other two hydroxy groups combine to form a 1-lower alkoxy-lower alkylidenedioxy group, a benzylidenedioxy group, a phosphinicodioxy group, or a carbonyldioxy group together with the protecting groups thereof. However, the protecting groups for the hydroxy groups of the β-D-glucopyranosyl group should not be construed to be limited to the above protecting groups, and may be any ones which can be removed after administering the present compound into the living body and give the hydroxy groups of the β-D-glucopyranosyl group, or can promote the absorption of the desired compound into the living body, or make it more easy to administer the present compound into the living body, or can increase the solubility in oil and/or water of the present compound.

When the hydroxy group of the β-D-glucopyranosyl group is acylated, the acyl group is preferably a lower alkanoyl group, a lower alkoxy-lower alkanoyl group, a lower alkoxycarbonyl group, a lower alkoxy-lower alkoxycarbonyl group, or an arylcarbonyl group (e.g., benzoyl group), or an amino acid residue which is obtained by removing a hydroxy group from the carboxyl group of a corresponding amino acid (wherein amino groups and/or carboxyl groups and/or hydroxy groups in said residue may be protected by a conventional protecting group). The amino acid residue includes a group which is obtained by removing a hydroxy group from the carboxyl group of a natural amino acid such as aspartic acid, glutamic acid, glutamine, serine, sarcosine, proline, phenylalanine, leucine, isoleucine, glycine, tryptophan, cysteine, histidine, tyrosine, or valine, or an antipode thereof, or a racemic compound thereof.

When Z is a β-D-glucopyranosyl group wherein two hydroxy groups of the β-D-glucopyranosyl group combine to form a 1-lower alkoxy-lower alkylidenedioxy group, a benzylidenedioxy group, a phosphinicodioxy group, or a carbonyldioxy group together with the protecting groups thereof, said β-D-glucopyranosyl group may be a β-D-glucopyranosyl group wherein the 4- and 6-hydroxy groups of the β-D-glucopyranosyl group combine to form a 1-lower alkoxy-lower alkylidenedioxy group, a benzylidenedioxy group, a phosphinicodioxy group, or a carbonyldioxy group together with the protecting groups thereof. Such β-D-glucopyranosyl group has the formula:

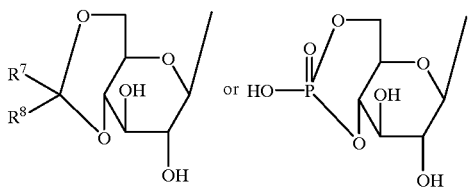

wherein one of $R^7$ and $R^8$ is a hydrogen atom or a lower alkyl group, and the other is a lower alkoxy group, or one of $R^7$ and $R^8$ is a hydrogen atom, and the other is a phenyl group, or $R^7$ and $R^8$ combine to form an oxo group.

When two hydroxy groups of the β-D-glucopyranosyl group combine to form a 1-lower alkoxy-lower alkylidenedioxy group together with the protecting groups thereof, the 1-lower alkoxy-lower alkylidenedioxy group is preferably a 1-lower alkoxyethylidenedioxy group, and more preferably a 1-methoxyethylidenedioxy group or a 1-ethoxyethylidenedioxy group.

Y of the formula (I) is preferably an alkyl group having 1 to 4 carbon atoms, more preferably a methyl group or an ethyl group.

Representative compounds of the present invention are compounds of the formula (I) wherein Z is a β-D-glucopyranosyl group wherein one or more hydroxy groups may optionally be acylated by a group selected from a lower alkanoyl group, a lower alkoxycarbonyl group, a lower alkoxy-lower alkanoyl group and a lower alkoxy-lower alkoxycarbonyl group, or a β-D-glucopyranosyl group wherein two hydroxy groups combine to form a 1-lower alkoxy-lower alkylidenedioxy group or a phosphinicodioxy group together with the protecting groups thereof.

More specifically, representative compounds of the present invention are compounds of the formula (I) wherein Z is a β-D-glucopyranosyl group wherein the 2-hydroxy group, or the 2- and the 3-hydroxy groups, or the 4-hydroxy group, or the 6-hydroxy group may optionally be acylated by a group selected from a lower alkanoyl group, a lower alkoxycarbonyl group, a lower alkoxy-lower alkanoyl group, and a lower alkoxy-lower alkoxycarbonyl group, or a β-D-glucopyranosyl group wherein the 4- and the 6-hydroxy groups combine to form a 1-lower alkoxy-lower alkylidenedioxy group or a phosphinicodioxy group together with the protecting groups thereof.

Among the compounds (I) of the present invention, preferable compounds are compounds of the formula (I) wherein OX is a hydroxy group, a lower alkanoyloxy group, or a lower alkoxycarbonyloxy group, Z is a β-D-glucopyranosyl group, a 2-O-(lower alkanoyl)-β-D-glucopyranosyl group, a 2,3-di-O-(lower alkanoyl)-β-D-glucopyranosyl group, a 4-O-(lower alkoxycarbonyl)-β-D-glucopyranosyl group, a 6-O-(lower alkanoyl)-β-D-glucopyranosyl group, a 6-O-(lower alkoxycarbonyl)-β-D-glucopyranosyl group, a 6-O-(lower alkoxy-lower alkanoyl)-β-D-glucopyranosyl group, a 6-O-(lower alkoxy-lower alkoxycarbonyl)-β-D-glucopyranosyl group, a 4,6-O-(1-lower alkoxy-lower alkylidene)-β-D-glucopyranosyl group, or 4,6-O-phosphinico-β-D-glucopyranosyl group.

More preferable compounds are compounds of the formula (I) wherein OX is a hydroxy group or a lower alkanoyloxy group, Z is a β-D-glucopyranosyl group, a 2,3-di-O-(lower alkanoyl)-β-D-glucopyranosyl group, a 4-O-(lower alkoxycarbonyl)-β-D-glucopyranosyl group, a 6-O-(lower alkoxycarbonyl)-β-D-glucopyranosyl group, a 4,6-O-(1-lower alkoxy-lower alkylidene)-β-D-glucopyranosyl group, or a 4,6-O-phosphinico-β-D-glucopyranosyl group.

Among the present compounds (I), further preferable compounds are compounds of the formula (I) wherein OX is a hydroxy group, Y is a methyl group or an ethyl group, Z is a β-D-glucopyranosyl group, a 4-O-(lower alkoxycarbonyl)-β-D-glucopyranosyl group, a 6-O-(lower alkoxycarbonyl)-β-D-glucopyranosyl group, a 4,6-O-(1-lower alkoxy-lower alkylidene)-β-D-glucopyranosyl group, or a 4,6-O-phosphinico-β-D-glucopyranosyl group.

Especially preferable compounds are compounds of the formula (I) wherein Z is a β-D-glucopyranosyl group or a 6-O-(lower alkoxycarbonyl)-β-D-glucopyranosyl group.

The propiophenone derivatives (I) of the present invention may be used for the purpose of the present invention either in the free form or in the form of a pharmaceutically acceptable salt thereof. The pharmaceutically acceptable salt may be an alkali metal salt (e.g., sodium salt), a salt with an inorganic acid (e.g., hydrochloride), or a salt with an organic acid (e.g., tosylate).

The propiophenone derivatives (I) of the present invention or a pharmaceutically acceptable salt thereof includes an intramolecular salt thereof, or a solvate or hydrate thereof, as well.

The compounds (I) of the present invention or a pharmaceutically acceptable salt thereof may be administered either orally or parenterally, and may be formulated into a pharmaceutical preparation in admixture with a pharmaceutically acceptable carrier or diluent suitable for oral administration or parenteral administration. The pharmaceutically acceptable carrier or diluent may be, for example, binders (e.g., syrup, gum arabic, gelatin, sorbitol, tragacanth, polyvinylpyrrolidone, etc.), excipients (e.g., lactose, sucrose, corn starch, potassium phosphate, sorbitol, glycine, etc.), lubricants (e.g., magnesium stearate, talc, polyethylene glycol, silica, etc.), disintegrators (e.g., potato starch, etc.), wetting agents (e.g., sodium laurylsulfate, etc.), and the like. These pharmaceutical preparations may be in the form of a solid preparation such as tablets, granules, capsules, powders, etc., or in the form of a liquid preparation such as solution, suspension, emulsion, etc., when administered orally. When administered parenterally, the pharmaceutical preparations may be in the form of suppository, an injection preparation or an intravenous drip preparation using distilled water for injection, a physiological salt solution, an aqueous glucose solution, and so on.

The dose of the propiophenone derivative (I) or a pharmaceutically acceptable salt thereof varies depending on the administration routes, ages, weights and conditions of patients, or severity of diseases to be cured, but it may be in the range of from 0.05 to 30 mg/kg/day, preferably in the range of from 0.5 to 15 mg/kg/day in case of oral administration. In case of parenteral administration, the dose of the present compound (I) may be in the range of from 0.005 to 30 mg/kg/day, preferably in the range of from 0.05 to 3 mg/kg/day.

The desired compound (I) of the present invention may be prepared by reducing a compound of the formula (II):

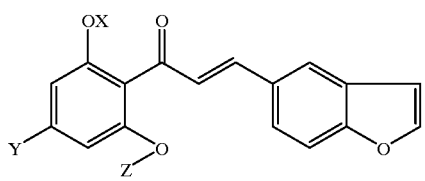

(II)

wherein the symbols are the same as defined above, and if necessary, followed by converting the product into a pharmaceutically acceptable salt thereof.

The reduction reaction may be carried out by a conventional method such as reduction with a metal hydride, catalytic reduction, etc. For example, the reduction with a metal hydride may be carried out by using a metal hydride in a solvent, and the catalytic reduction may be carried out by using a catalyst under atmospheric pressure of hydrogen gas in a solvent.

In the catalytic reduction, the catalyst may be any conventional one, for example, palladium-carbon, platinum-carbon, platinum oxide, Raney nickel. In order to prevent the over reduction of the double bond of the benzofuran ring, there may be added a substance which can reduce the catalytic ability of the catalyst, for example, amines such as 4-(N,N-dimethylamino)pyridine, N,N-dimethylaniline, aniline, dipropylamine, diisopropylamine, morpholine, piperazine, dicyclohexylamine, piperidine, pyrrolidine, or amides such as N,N-dimethylacetamide.

In the reduction with a metal hydride, the metal hydride may be any one which can reduce a carbon—carbon double bond. However, it may be preferable to use metal hydrides which do not reduce a ketone, for example, sodium tellurium hydride (NaTeH), which is prepared according to the method disclosed in Synthesis, p. 545 (1978). Sodium tellurium hydride is usually used in an amount of 1 to 3 mole equivalents, preferably in an amount of 1 to 1.5 mole equivalents, to 1 mole equivalent of the compound (II).

In the reduction reaction, the solvent may be any one which does not disturb the reaction, for example, an organic solvent such as alcohols (e.g., methanol, ethanol), ethers (e.g., tetrahydrofuran), esters (e.g., ethyl acetate), organic acids (e.g., acetic acid), or a mixture of such organic solvents and water.

The reduction reaction may be carried out from a temperature under cooling to a temperature with heating, preferably at a temperature of from 10° C. to 30° C.

The compounds (I) of the present invention thus obtained can be converted into each other by the following processes, or a combined process thereof.

(1) Among the present compounds (I), the compound of the formula (I-b):

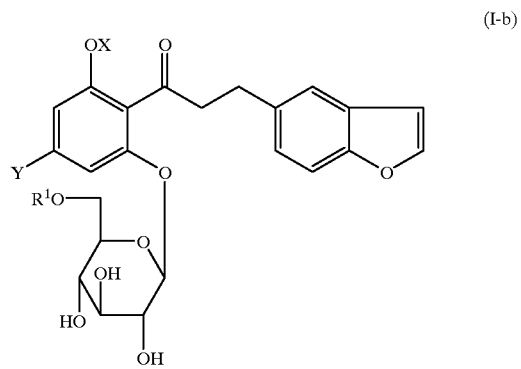

(I-b)

wherein $R^1$ is an acyl group, and the other symbols are the same as defined above, can be prepared by acylating the compound of the formula (I-a) of the present invention:

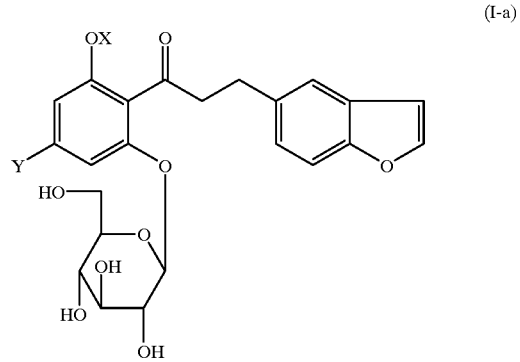

(I-a)

wherein the symbols are the same as defined above.

(2) Among the present compounds (I), the compound of the formula (I-c):

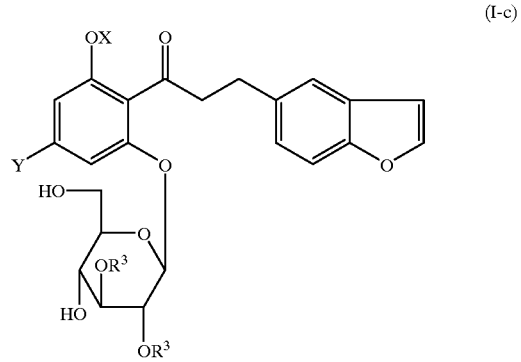

(I-c)

wherein $R^3$ is an acyl group, and the other symbols are the same as defined above, can be prepared by acylating a compound of the formula (I-d), which is a compound of the formula (I-a) wherein the 4- and the 6-hydroxy groups of the β-D-glucopyranosyl group are protected:

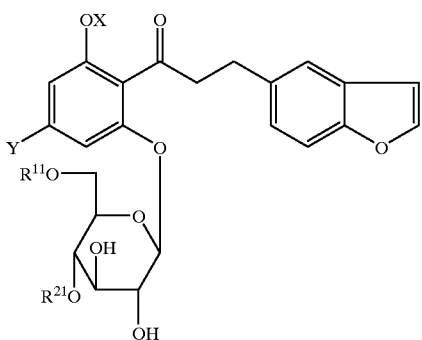
(I-d)

wherein $R^{11}O$ and $R^{21}O$ are protected hydroxy groups, and the other symbols are the same as defined above, followed by removing the protecting groups, i.e., $R^{11}$ and $R^{21}$, from the product.

(3) Among the present compounds (I), the compound of the formula (I-e):

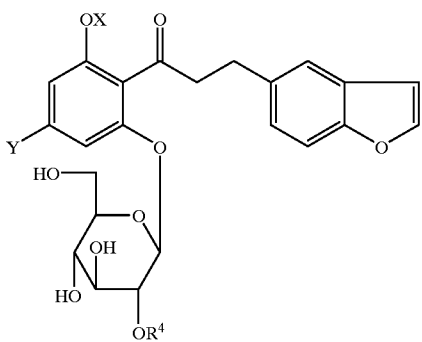
(I-e)

wherein $R^4$ is an acyl group, and the other symbols are the same as defined above, can be prepared by acylating a compound of the formula (I-f), which is a compound of the formula (I-d) wherein the 3-hydroxy group of the β-D-glucopyranosyl group is further protected:

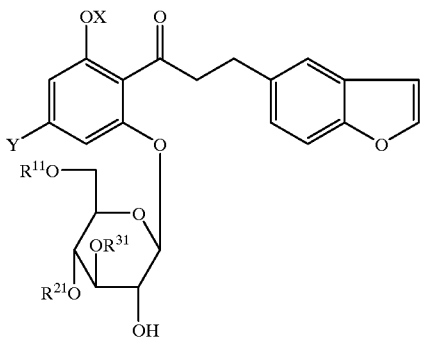
(I-f)

wherein $R^{31}O$ is a protected hydroxy group, and the other symbols are the same as defined above, followed by removing the protecting groups, i.e., $R^{11}$, $R^{21}$, and $R^{31}$, from the product.

In the compounds (I-d) and (I-f), the protecting groups $R^{11}$, $R^{21}$, and $R^{31}$ for the hydroxy groups of the β-D-glucopyranosyl group may be any conventional one, and the protecting groups for the 4- and the 6-hydroxy groups are preferably ones which can combine each other to form a benzylidene group, etc. The protecting group for the 3-hydroxy group is preferably a tri-lower alkylsilyl group (e.g., t-butyldimethylsilyl group, trimethylsilyl group). The removal of these protecting groups is carried out by a conventional method such as acid-treatment, hydrolysis, reduction, etc.

The acylation reaction of the above processes (1), (2) and (3) is carried out by reacting the starting compound with an organic acid (e.g., a lower alkanecarboxylic acid such as acetic acid, a lower alkoxy-lower alkanecarboxylic acid such as methoxy acetic acid, benzoic acid, etc.) corresponding to the desired acyl group, or a salt thereof, or a reactive derivative thereof.

The reaction between the organic acid corresponding to the desired acyl group, or a salt thereof, and the starting compound is carried out in a suitable solvent in the presence or absence of a condensing agent. The reaction between the reactive derivative of the organic acid and the starting compound is carried out in a suitable solvent or without a solvent in the presence or absence of an acid acceptor.

The salt of the organic acid includes, for example, an alkali metal salt or an alkaline earth metal salt such as sodium salt, potassium salt, calcium salt, etc. When these salts of the organic acid are used in the condensation reaction, these salts may preferably be used after prepared to be in the form of a free acid.

The reactive derivative of the organic acid includes, for example, an acid halide, acid anhydride, active ester, or active amide of a lower alkanecarboxylic acid, lower alkoxy-lower alkanecarboxylic acid, lower alkoxycarboxylic acid, benzoic acid, etc.

The condensing agent may be any conventional ones, for example, dicyclohexylcarbodiimide, diethyl cyanophosphate, carbonyldiimidazole, bis(2-oxo-3-oxazolidinyl)phosphinic chloride, etc.

The acid acceptor may be any conventional one, for example, an inorganic base such as an alkali metal hydroxide (e.g., sodium hydroxide, potassium hydroxide, etc.); an alkali metal carbonate (e.g., potassium carbonate, sodium carbonate, etc.); an alkali metal hydrogen carbonate (e.g., sodium hydrogen carbonate, potassium hydrogen carbonate, etc.); an alkali metal hydride (e.g., sodium hydride, potassium hydride, etc.), or an organic base such as a tri-lower alkylamine (e.g., triethylamine, diisopropylethylamine, etc.); pyridine; 2,4,6-collidine; 4-(N,N-dimethylamino) pyridine; quinuclidine; aniline; N,N-dimethylaniline, etc.

The solvent may be any conventional one which does not disturb the reaction, for example, water; esters (e.g., ethyl acetate); halogenated hydrocarbons (e.g., dichloromethane); amides (e.g., dimethylformamide); ethers (e.g., tetrahydrofuran); nitrites (e.g., acetonitrile); etc., or a mixture thereof. Beside, an organic base such as pyridine, 2,4,6-collidine, etc. which are exemplified above as an acid acceptor may be also used as a solvent.

The reaction may be carried out from a temperature under cooling to a temperature with heating, preferably at a temperature from −10° C. to 100° C., especially at a temperature of from 0° C. to 50° C.

In the above process (1), the compound of the formula (I-b) wherein $R^1$ is a lower alkoxycarbonyl group can be prepared by a modified method disclosed in J. Chem. Soc. Perkin Trans. 1, p. 589 (1993), i.e., by reacting the compound (I-a) with the di-lower alkyl carbonate in the presence or absence of molecular sieves in a suitable solvent with using a lipase.

The lipase may preferably be a lipase derived from *Candida antarctica*, for example, Novozym 435 (manufactured by Novo Nordisk A/S).

The solvent may be any conventional one which does not disturb the reaction, and preferably be ethers such as dioxane, ethyleneglycol diethyl ether, etc.

The compound (I-a) is prepared by reduction of the compound of the formula (II) wherein Z is a β-D-glucopyranosyl group, and the compound (I-a) is useful as one of the compounds of the present invention as well as a synthetic intermediate for preparing other compounds of the present invention.

The compound (I-d) is prepared by protecting the 4- and the 6-hydroxy groups of the β-D-glucopyranosyl group of the compound (I-a). The compound (I-f) is prepared by protecting the 3-hydroxy group of the β-D-glucopyranosyl group of the compound (I-d). The protection of the hydroxy groups of the β-D-glucopyranosyl group is carried out by a method disclosed in the process (5) described hereinbelow, or by the methods disclosed in Examples, or a conventional method.

In the acylation reaction of the above processes (1), (2) and (3), when OX of the starting compounds is a hydroxy group, the OX may optionally be acylated as well, and the product thus obtained, i.e., the product wherein OX is acylated, is also included in the present invention. When OX of the starting compounds should not be acylated, the product wherein OX is acylated is treated in a suitable solvent (e.g., tetrahydrofuran, methanol, water, etc.) with a base such as an alkali metal hydrogen carbonate (e.g., sodium hydrogen carbonate, potassium hydrogen carbonate, etc.), amines (e.g., t-butylamine, etc.) to remove the acyl group of the product.

(4) Among the compounds (I) of the present invention, the compound of the formula (I-g):

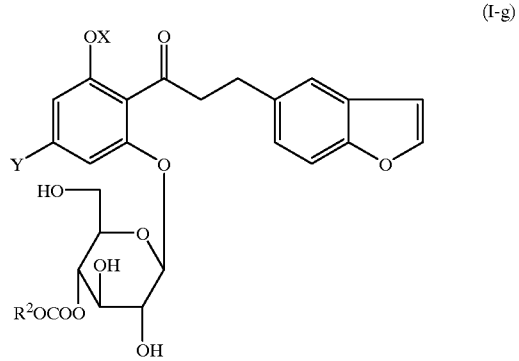

(I-g)

wherein $R^2$ is a lower alkyl group, and the other symbols are the same as defined above, can be prepared by reacting a compound of the formula (I-h):

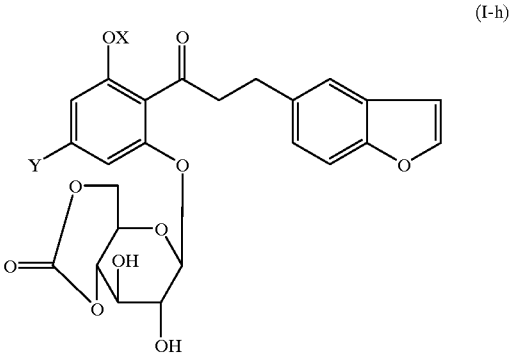

(I-h)

wherein the symbols are the same as defined above, with a compound of the formula (III):

$$R^2OH \qquad (III)$$

wherein $R^2$ is the same as defined above.

The reaction is carried out in a suitable solvent in the presence or absence of an acid catalyst.

The compound (III) may be a straight chain or branched chain alkanol having 1 to 6 carbon atoms such as methanol, ethanol, propanol, isopropanol, n-butanol, t-butanol, etc., and is preferably used in an equimolar amount or in a slightly excess amount, to the amount of the compound (I-h).

The solvent may be any one which does not disturb the reaction, for example, halogenated hydrocarbons (e.g., dichloromethane, dichloroethane, chloroform, etc.). The compound (III) per se can be used as a solvent.

The acid catalyst includes, for example, organic acids such as an arylsulfonic acid (e.g., p-toluenesulfonic acid), a lower alkanesulfonic acid (e.g., methanesulfonic acid, ethanesulfonic acid), a lower alkanecarboxylic acid (e.g., acetic acid), or an inorganic acid such as hydrochloric acid, sulfuric acid.

The reaction is carried out from a temperature under cooling to a temperature with heating, preferably at a temperature of from 25° C. to 50° C., especially at a temperature of from 25° C. to 35° C.

Besides, the compound (I-h) can be prepared (a) by reacting the compound (I-a) with an aryl halogenoformate (e.g., p-nitrophenyl halogenoformate) or N,N-carbonyldiimidazole, etc., in a solvent or without a solvent in the presence or absence of an acid acceptor, if necessary, under heating; or (b) by the process (5) described hereinbelow.

In the above (a), the solvent may be any one which does not disturb the reaction, for example, tetrahydrofuran, dichloromethane, chloroform, etc.

The acid acceptor includes, for example, an organic base (e.g., 2,4,6-collidine, pyridine, 2,6-lutidine), or an inorganic base (e.g., sodium hydrogen carbonate). When an organic base is used as an acid acceptor, the organic base per se can be used as a solvent.

The reaction is carried out from a temperature under cooling to a temperature with heating, especially at a temperature of from –50° C. to 60° C. When an aryl halogenoformate is used in the reaction, it is preferable to heat the reaction system after the aryl halogenoformate is added thereto, especially preferable to heat it at 40° C. to 70° C.

(5) Among the present compounds (I), the compound of the formula (I-i):

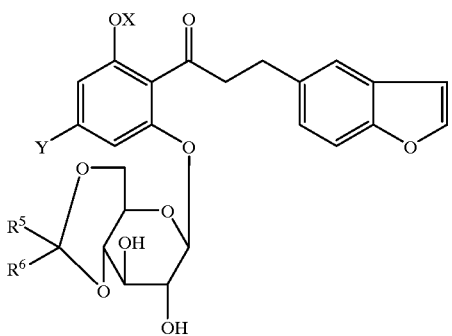

(I-i)

wherein $R^5$ is a hydrogen atom or a lower alkyl group and $R^6$ is a lower alkoxy group, or $R^5$ is a hydrogen atom and $R^6$ is a phenyl group, or $R^5$ and $R^6$ may combine to form an oxo group, and the other symbols are the same as defined above, can be prepared by reacting a compound of the formula (I-a) with a compound of the formula (IV):

(IV)

wherein $A^1$ and $A^2$ are leaving groups, and the other symbols are the same as defined above.

In the compounds (IV), the leaving group may be any conventional one which does not disturb the reaction, for example, a halogen atom (e.g., chlorine atom, bromine atom), and a lower alkoxy group (e.g., methoxy, ethoxy).

The reaction is carried out in a suitable solvent or without a solvent in the presence or absence of an acid or a base.

The solvent may be any one which does not disturb the reaction, for example, halogenated hydrocarbons (e.g., dichloromethane, chloroform, dichloroethane, etc.), ethers (e.g., tetrahydrofuran, diethyl ether, etc.), or an excess amount of the compound (IV) can also be used as a solvent.

The acid includes, for example, an organic acid such as an arylsulfonic acid (e.g., p-toluenesulfonic acid), a lower alkanesulfonic acid (e.g., methanesulfonic acid, ethanesulfonic acid, etc.), trifluoroacetic acid, etc., or an inorganic acid such as hydrochloric acid, sulfuric acid, etc., or a salt of a strong acid and a weak base such as pyridinium p-toluenesulfonate.

The base includes, for example, a tri-lower alkylamine (e.g., triethylamine, diisopropylethylamine), pyridine, 4-(N, N-dimethylamino)pyridine, aniline, N,N-dimethylaniline, etc.

The reaction is carried out from a temperature under cooling to a temperature with heating, preferably at a temperature of from 0° C. to 50° C., especially at a temperature of from 20° C. to 30° C.

(6) Among the present compounds (I), the compound of the formula (I-j):

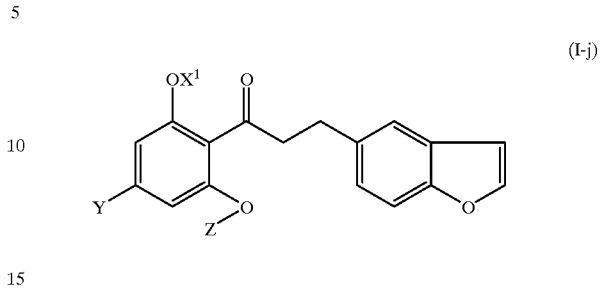

(I-j)

wherein $OX^1$ is a protected hydroxy group, and the other symbols are the same as defined above, and the compound of the formula (I-k):

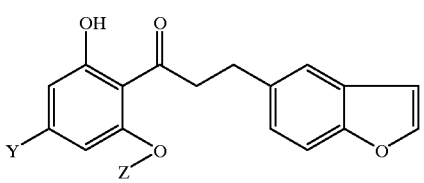

(I-k)

wherein the symbols are the same as defined above, can be converted each other. That is, the compound (I-j) is prepared by protecting the compound (I-k), and the compound (I-k) is prepared by removing the protecting group $X^1$ from the compound (I-j).

The protection of the compound (I-k) is carried out by a conventional method, for example, when protecting the compound (I-k) with an acyl group, the protection is carried out in the same manner as in the above processes (1), (2) and (3). When protecting the compound (I-k) with an allyl group, the protection is carried out by reacting the compound (I-k) in a suitable solvent (e.g., acetone) in the presence or absence of an acid acceptor (e.g., potassium carbonate) with an allyl halide (e.g., allyl bromide).

The removal of the protecting group $X^1$ from the compound (I-j) is carried out by a conventional method which should be selected according to the types of the protecting group to be removed. For example, when $OX^1$ is a lower alkanoyloxy group or a lower alkoxycarbonyloxy group, the removal of the protecting group is carried out by treating with an acid or a base in a suitable solvent. When $OX^1$ is a lower alkoxy-lower alkoxy group, the removal of the protecting group is carried out in a suitable solvent with using an acid. When $OX^1$ is an allyloxy group, the removal of the protecting group is carried out by treating with a palladium catalyst (e.g., dichlorobis(triphenylphosphine)-palladium (II)) in a suitable solvent (e.g., acetonitrile) in the presence of ammonium formate.

(7) Among the present compounds (I), the compound of the formula (I-l):

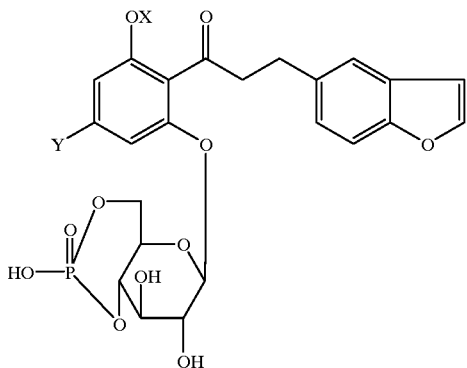

(I-l)

wherein the symbols are the same as defined above, can be prepared by subjecting a compound of the formula (I-m):

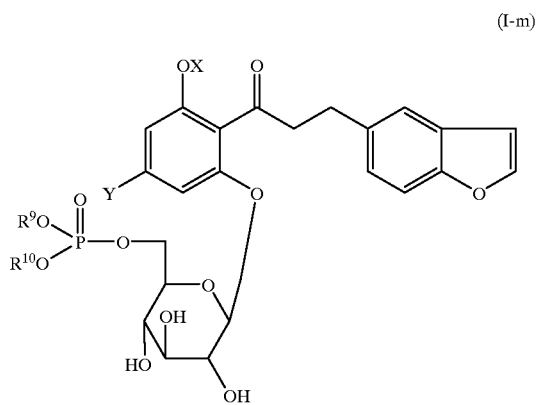

(I-m)

wherein $R^9$ and $R^{10}$ are the same or different and each protecting groups for hydroxy group, and the other symbols are the same as defined above, to hydrolysis.

The protecting groups $R^9$ and $R^{10}$ may be any conventional protecting groups, and preferably a phenyl group, a lower alkyl group (e.g., methyl, ethyl), etc.

The hydrolysis is carried out by a conventional method, but preferably carried out in a solvent or without a solvent in the presence of a base.

The solvent may be any one which does not disturb the reaction, for example, ethers (e.g., tetrahydrofuran, dioxane, etc.), water, or a mixture of these solvents.

The base includes, for example, an alkali metal hydroxide (e.g., lithium hydroxide, sodium hydroxide, potassium hydroxide, etc.), and an alkali metal carbonate (e.g., lithium carbonate, sodium carbonate, potassium carbonate, etc.).

The reaction is carried out from a temperature under cooling to a temperature with heating, preferably at a temperature of from −20° C. to 50° C., more preferably at a temperature of from 0° C. to 30° C.

When the hydrolysis is carried out with using a base, the obtained compound (I-e) is isolated in the form of a salt with the base to be used in the hydrolysis.

The compound (I-m) can be prepared by reacting the compound (I-a) with a compound of the formula (VIII):

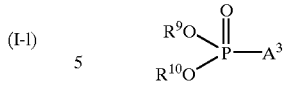

(VIII)

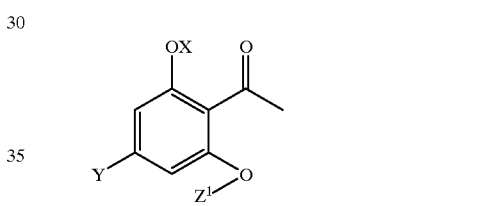

wherein $A^3$ is a leaving group, and the other symbols are the same as defined above.

In the compound (VIII), the leaving group $A^3$ may be any conventional one which does not disturb the reaction, and preferably a halogen atom (e.g., chlorine, bromine).

The reaction is carried out in a suitable solvent or without a solvent in the presence or absence of a base.

The solvent may be any conventional one which does not disturb the reaction, for example, halogenated hydrocarbons (e.g., dichloromethane, chloroform, dichloroethane, etc.), ethers (e.g., tetrahydrofuran, diethyl ether, etc.).

The base includes, for example, a tri-lower alkylamine (e.g., triethylamine, diisopropylethylamine), pyridine, 4-(N, N-dimethylamino)pyridine, aniline, N,N-dimethylaniline, 2,4,6-collidine, etc.

The reaction is carried out from a temperature under cooling to a temperature with heating, preferably at a temperature of from −20° C. to 50° C., more preferably at a temperature of from 0° C. to 30° C.

The staring compound (II) of the present invention may be prepared by condensing a compound of the formula (V)

(V)

wherein $Z^1$ is a β-D-glucopyranosyl group wherein the hydroxy groups may optionally be protected, and the other symbols are the same as defined above, with 5-formylbenzo[b]furan, and if necessary, followed by protecting the hydroxy groups of the product.

When $Z^1$ of the starting compound (V) is a β-D-glucopyranosyl group wherein the hydroxy groups are protected, the protecting groups for the hydroxy groups of the β-D-glucopyranosyl group may be any conventional protecting group for hydroxy group, for example, a lower alkanoyl group (e.g., acetyl group).

The condensation reaction of the starting compound (V) with 5-formylbenzo[b]furan may be carried out by the conventional method, for example, in a suitable solvent (e.g., an organic solvent such as methanol, ethanol, etc. or a mixture of these organic solvents and water), in the presence of a base (e.g., alkali metal hydroxides such as potassium hydroxide), from a temperature under cooling to a temperature with heating (especially at a temperature of from 10° C. to 30° C.).

When protecting the hydroxy groups of the product thus obtained, the protection is carried out by a conventional method, or a method disclosed in the above processes (1) to (5), or a combined process of these processes.

The compound (II) obtained in the above process can be used in the reduction reaction of the present invention with being further purified, but can be used without purification.

The compound (V) for preparing the compound (II) is prepared by condensing a compound of the formula (VI):

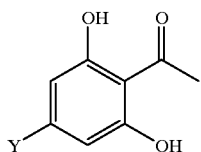
(VI)

wherein the symbol is the same as defined above, with 2,3,4,6-tetra-O-acetyl-α-D-glucopyranosyl bromide with adding a base in the presence or absence of a quaternary ammonium salt in a suitable solvent, and if necessary, followed by protecting the 6'-phenolic hydroxyl group of the product.

The solvent may be any one which does not disturb the reaction, for example, halogenated hydrocarbons (e.g., chloroform), aromatic hydrocarbons (e.g., toluene), ketones (e.g., acetone), and water.

The quaternary ammonium salt may preferably be a tetra-lower alkylammonium halide, a tetra-lower alkylammonium hydrogen sulfate, a benzyl tri-lower alkylammonium halide, etc. Among them, benzyl tri-lower alkylammonium chloride is especially preferable.

The base includes, for example, an alkali metal hydroxide (e.g., sodium hydroxide, potassium hydroxide), an alkali metal carbonate (e.g., potassium carbonate, sodium carbonate), cadmium carbonate, etc. The reaction is carried out from a temperature under cooling to a temperature with heating.

The reaction is carried out, for example, (i) by reacting the compound (VI) with 2,3,4,6-tetra-O-acetyl-α-D-glucopyranosyl bromide in a suitable solvent (e.g., aqueous acetone) in the presence of potassium hydroxide, and if necessary, followed by protecting the hydroxy groups of the product, according to the method disclosed in J. Med. Pharm. Chem, 5, p. 1045 (1962); or (ii) by heating under reflux the compound (VI) with 2,3,4,6-tetra-O-acetyl-α-D-glucopyranosyl bromide in a suitable solvent (e.g., aromatic hydrocarbons such as toluene) in the presence of cadmium carbonate, and if necessary, followed by protecting the hydroxy groups of the product, according to the method disclosed in Carbohydrate Research, 70, p. 313 (1979); or (iii) by reacting the compound (VI) with 2,3,4,6-tetra-O-acetyl-α-D-glucopyranosyl bromide in a suitable solvent (e.g., halogenated hydrocarbons such as chloroform, or adding thereto a small amount of water) in the presence of a quaternary ammonium salt (e.g., benzyltributylammonium chloride) and an alkali metal carbonate (e.g., potassium carbonate), and if necessary, followed by protecting the hydroxy groups of the product.

The protection of the 6'-phenolic hydroxy group is carried out by a conventional method.

The compound of the formula (VI) wherein Y is a methyl group is prepared by the method disclosed in J. Org. Chem., 29, p. 2800 (1964), or by acetylating orcinol, followed by subjecting the resulting orcinol diacetate to Freis rearrangement in a suitable solvent (e.g., chlorobenzene) or without a solvent in the presence of a Lewis acid (e.g., aluminum chloride).

The compound of the formula (VI) wherein Y is a lower alkyl group having two or more carbon atoms is prepared by the following scheme.

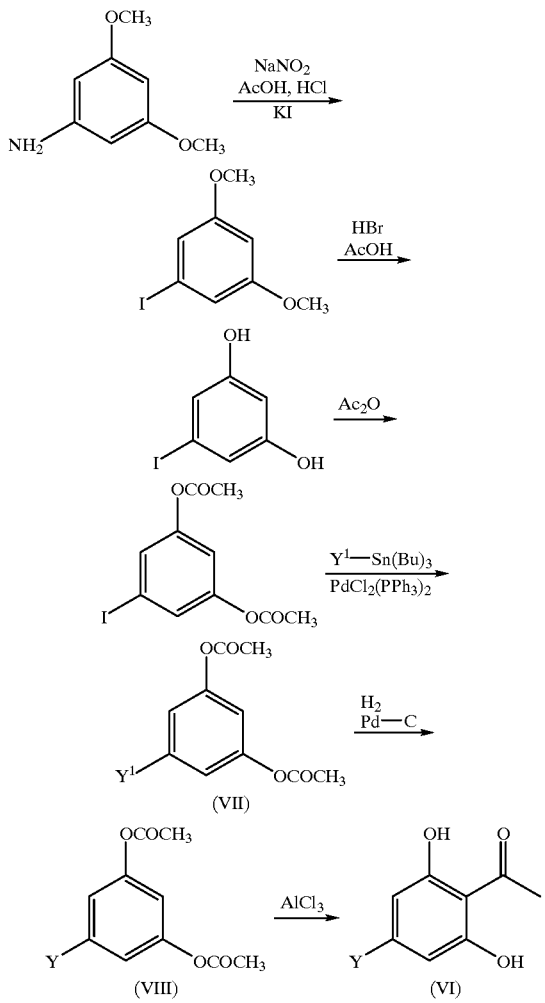

wherein $Y^1$ is a lower alkenyl group, and the other symbols are the same as defined above.

That is, the compound (VI) is prepared by the following steps:
(i) converting 3,5-dimethoxyaniline into a diazonium salt thereof with using sodium nitrite in acetic acid in the presence of a hydrochloric acid, and reacting the product with potassium iodide to give dimethoxyiodobenzene;
(ii) treating the dimethoxyiodobenzene in acetic acid with hydrobromic acid to de-methylation;
(iii) acetylating the phenolic hydroxy groups of the product with using acetic anhydride, etc. to give diacetoxyiodobenzene;
(iv) reacting the diacetoxyiodobenzene with tri-butyl-lower alkenyl tin in the presence of a palladium catalyst (e.g., dichlorobis(triphenylphosphine) palladium (II)) to give the diacetoxy-lower alkenylbenzene of the formula (VII);
(v) subjecting the compound (VII) to catalytic reduction to give the diacetoxy-lower alkylbenzene of the formula (VIII);
(vi) subjecting the compound (VIII) to Freis rearrangement in the presence of a Lewis acid such as aluminum chloride.

The diacetoxy-lower alkylbenzene (VIII) is also prepared as follows.

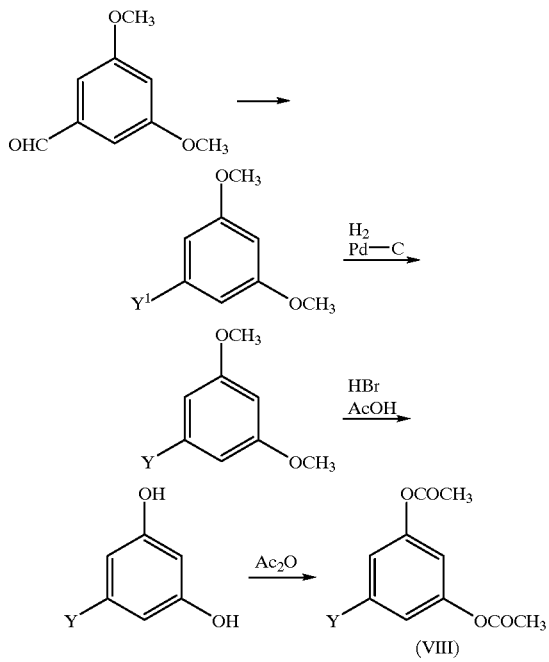

wherein the symbols are the same as defined above.

That is, the compound (VIII) is prepared by the following steps:

(i) subjecting the 3,5-dimethoxybenzaldehyde to Wittig reaction, etc. to give the dimethoxy-lower alkenylbenzene;

(ii) subjecting the resulting dimethoxy-lower alkenylbenzene to catalytic reduction to give the dimethoxy-lower alkylbenzene;

(iii) treating the dimethoxy-lower alkylbenzene with hydrobromic acid in acetic acid to de-methylation to give dihydroxy-lower alkylbenzene;

(iv) acetylating the dihydroxy-lower alkylbenzene with acetic anhydride, etc., to give the compound (VIII).

In the present description and the claims, the lower alkyl group means a straight chain or branched chain alkyl group having 1 to 6 carbon atoms, for example, methyl, ethyl, propyl, butyl, etc., preferably ones having 1 to 4 carbon atoms. The lower alkoxy group means a straight chain or branched chain alkoxy group having 1 to 6 carbon atoms, for example, methoxy, ethoxy, propoxy, butoxy, etc., preferably ones having 1 to 4 carbon atoms. The lower alkanoyl group means a straight chain or branched chain alkanoyl group having 2 to 6 carbon atoms, for example, acetyl, propionyl, butyryl, etc., preferably ones having 2 to 4 carbon atoms. The lower alkylidene group means a straight chain or branched chain alkylidene group having 1 to 6 carbon atoms, for example, methylidene, ethylidene, isopropylidene, etc., preferably ones having 1 to 4 carbon atoms.

Throughout the present description and the claims, the β-D-glucopyranosyl group has the following structure:

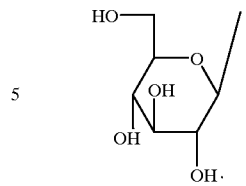

EXAMPLES

The present invention is illustrated by the following Examples and Reference Examples, but should not be construed to be limited thereto.

Example 1

2'-(2,3,4,6-Tetra-acetyl-β-D-glucopyranosyloxy)-6'-hydroxy-4'-methylacetophenone (120 g) is dissolved in a chilled mixture of ethanol (1.2 l) and 50% aqueous potassium hydroxide solution (240 g), and thereto is added 5-formylbenzo[b]furan (42.4 g), and the mixture is stirred at room temperature overnight under argon atmosphere. To the reaction solution are added 4-dimethylaminopyridine (29.5 g) and 10% platinum-carbon (23.58 g), and the mixture is stirred at room temperature for 4.5 hours under atmospheric pressure of hydrogen gas. The catalyst is removed by filtration, and the filtrate is washed with toluene, and acidified with 18% hydrochloric acid under ice-cooling. The mixture is extracted with ethyl acetate, and the organic layer is washed successively with water, a saturated aqueous sodium hydrogen carbonate solution, and a saturated aqueous sodium chloride solution. The washed aqueous layer is extracted with ethyl acetate, and the organic layers are combined, dried, and concentrated under reduced pressure. The residue is crystallized from water-ethanol to give 3-(5-benzo[b]furanyl)-2'-(β-D-glucopyranosyloxy)-6'-hydroxy-4'-methylpropiophenone (82.4 g).

m.p. 152.5–154° C.

ESI-MS (m/z): 476 [(M+NH$_4$)$^+$]

IR (nujol, cm$^{-1}$): 3560, 3510, 3350, 3270, 1630

NMR (DMSO-d$_6$) δ: 2.24 (3H, s), 3.00 (2H, t, J=7.4, the unit of 1, coupling constant, is Hz, hereinafter, the same), 3.1–3.5 (7H, m), 3.71(1H, ddd, f=2.0, 5.5, 12), 4.59 (1H, t, J=5.8), 4.98 (1H, d, J=7.3), 5.05 (1H, d, J=5.1), 5.12 (1H, d, J=4.6), 5.29 (1H, d, J=5.1), 6.40 (1H, d, J=0.4), 6.54 (1H, s), 6.88 (1H, dd, J=0.9, 2.2), 7.22 (1H, dd, J=1.8, 8.4), 7.46 (1H, d, J=8.6), 7.53 (1H, d, J=1.5), 7.93 (1H, d, J=2.2), 11.90 (1H, s)

Example 2

(1) 3-(5-Benzo[b]furanyl)-2'-(β-D-glucopyranosyloxy)-6'-hydroxy-4'-methylpropiophenone (2.50 g) is dissolved in acetone (20 ml), and thereto are added potassium carbonate (2.13 g) and allyl bromide (933 mg), and the mixture is refluxed for 6 hours. After cooling, the reaction mixture is poured into ice-water, and the mixture is extracted with ethyl acetate. The organic layer is washed with water, dried, and concentrated under reduced pressure. The resulting residue is purified by silica gel column chromatography (solvent; chloroform/methanol) to give 3-(5-benzo[b]furanyl)-2'-(β-D-glucopyranosyloxy)-6'-allyloxy-4'-methylpropiophenone (1.63 g).

ESI-MS (m/z): 521 [(M+Na)$^+$], 516 [(M+NH$_4$)$^+$]

IR (neat, cm$^{-1}$): 3019, 1691, 1609

NMR (DMSO-d$_6$) δ: 2.28 (3H, s), 2.92–3.02 (2H, m), 3.04–3.32 (6H, m), 3.40–3.50 (1H, m), 3.66–3.74 (1H, m), 4.50 (2H, dt, J=1.5, 5.0), 4.57 (2H, t(br)), 4.87 (1H, d, J=7.7), 5.03 (1H, d, J=4.8), 5.09 (1H, d(br)), 5.16 (1H, ddt, J=10.4, 1.7, 1.5), 5.23 (1H, br), 5.26 (1H, ddt, J=17.4, 1.7, 1.5), 5.90 (1H, ddt, J=17.4, 10.4,5.0), 6.56 (1H, s), 6.66 (1H, s), 6.88 (1H, dd, J=0.9, 2.2), 7.18 (1H, dd, J=1.7, 8.4), 7.45 (1H, d, J=8.4), 7.49 (1H, d, J=1.3), 7.93 (1H, d, J=2.2)

(2) 3-(5-Benzo[b]furanyl)-2'-(β-D-glucopyranosyloxy)-6'-allyloxy-4'-methylpropiophenone (500 mg) is dissolved in 2,4,6-collidine (5 ml), and the mixture is cooled to 40° C. with dry ice-acetone, and thereto is added dropwise a solution of methyl chloroformate (114 mg) in dichloromethane (0.5 ml) with stirring. The mixture is stirred at 40° C. for one hour, and stirred at room temperature for 1.5 hour. The reaction mixture is poured into cold 10% aqueous citric acid solution, and the mixture is extracted with ethyl acetate. The organic layer is washed with water, dried, and concentrated under reduced pressure. The resulting residue is purified by silica gel column chromatography (solvent; chloroform/methanol) to give 3-(5-benzo[b]furanyl)-2'-(6-O-methoxycarbonyl-β-D-glucopyranosyloxy)-6'-allyloxy-4'-methylpropiophenone (487 mg).

ESI-MS (m/z): 579 [(M+Na)$^+$]

IR (neat, cm$^{-1}$): 3401, 1751, 1609

NMR (DMSO-d$_6$) δ: 2.27 (3H, s), 2.92–2.99 (2H, m), 3.02–3.32 (5H, m), 3.57–3.62 (1H, m), 3.64(3H, s), 4.13 (1H, dd, J=6.8,11.4),4.38 (1H, dd, J=1.7, 11.4), 4.50 (2H, dt, J=5.0, 1.5), 4.91 (1H, d, J=7.7),5.16 (1H, ddt, J=10.6,1.8, 1.5), 5.21 (1H, d, J=5.0), 5.26 (1H, ddt, J=17.4,1.7, 1.6),5.35 (2H, d, J=5.7),5.89 (1H, ddt, J=17.2, 10.6, 4.9), 6.57 (1H, s), 6.61 (1H, s), 6.87 (1H, dd, J=0.9, 2.2),7.16 (1H, dd, J=1.8, 8.4), 7.45 (1H, d, J=8.4), 7.47 (1H, s), 7.93 (1H, d, J=2.0)

(3) 3-(5-Benzo[b]furanyl)-2'-(6-O-methoxycarbonyl-β-D-glucopyranosyloxy)-6'-allyloxy-4'-methylpropiophenone (470 mg) is dissolved in acetonitrile (7 ml), and thereto are added dichlorobis(triphenylphosphine)-palladium (II) (17.7 mg,) and ammonium formate (319 mg), and the mixture is heated under reflux overnight. After cooling, the insoluble materials are removed by filtration, and the filtrate is concentrated. To the residue are added ethyl acetate and water, and the mixture is shaken. The organic layer is separated, washed with water, dried, and concentrated under reduced pressure. The residue is purified by silica gel column chromatography (solvent; chloroform/methanol) to give 3-(5-benzo[b]furanyl)-2'-(6-O-methoxycarbonyl-β-D-glucopyranosyloxy)-6'-hydroxy-4'-methylpropiophenone (370 mg).

ESI-MS (m/z): 539 [(M+Na)$^+$], 534 [(M+NH$_4$)$^+$]

IR (nujol, cm$^{-1}$): 3200–3500, 1714

NMR (DMSO-d$_6$) δ: 2.23 (33H, s), 2.99 (2H, t, J=7.4), 3.14–3.42 (5H, m), 3.65 (3H, s), 3.63–3.69 (1H, m), 4.16 (1H, dd, J=6.6,11.5),4.39 (1H, dd, J=2.0, 11.5), 5.02 (1H, d, J=7.5), 5.25 (1H, d, J=5.0), 5.37 (1H, d, J=5.3), 5.39 (1H, d, J=5.3), 6.42 (1H, s), 6.50 (1H, s), 6.88 (1H, dd, J=0.9, 2.2), 7.20 (1H, dd, J=1.7, 8.4), 7.47 (1H, d, J=8.4), 7.51 (1H, d, J=1.3), 7.93 (1H, d, J=2.2), 11.80 (1H, s)

Examples 3–9

(1) The corresponding starting compounds are treated in the same manner as in Example 2-(2) to give the compounds as listed in Tables 1–4.

TABLE 1

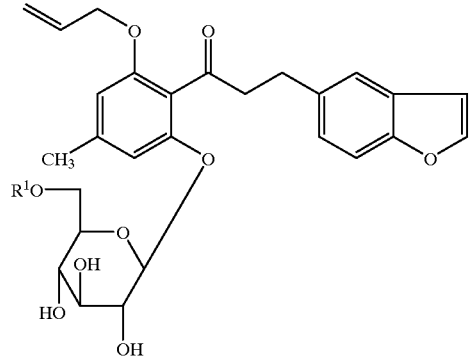

| Ex. No. | R$^1$ | Physicochemical properties |
|---|---|---|
| 3-(1) | CH$_3$CH$_2$OCO— | FAB-MS (m/z): 571 [(M+H)$^+$]<br>IR (neat, cm$^{-1}$): 3397, 1747, 1697, 1609<br>NMR (DMSO-d$_6$) δ: 1.15 (3H, t, J=7.1), 2.28 (3H, s), 2.92–2.99 (2H, m), 3.32–3.34 (5H, m), 3.61 (1H, m), 4.05 (2H, q, J=7.1), 4.11 (1H, dd, J=7.0, 11.7), 4.37 (1H, dd, J=1.7, 11.7), 4.55 (2H, dt, J=4.9, 1.5), 4.91 (1H, d, J=7.7), 5.16 (1H, ddt, J=10.6, 1.8, 1.5), 5.19 (1H, d, J=5.1), 5.25 (1H, ddt, J=17.4, 1.8, 1.7), 5.38 (2H, d, J=5.5), 5.89 (1H, ddt, J=17.2, 10.6, 4.9), 6.58 (1H, s), 6.63 (1H, s), 6.87 (1H, dd, J=0.9, 2.2), 7.16 (1H, dd, J=1.7, 8.6), 7.45 (1H, d, J=8.6), 7.47 (1H, m), 7.93 (1H, d, J=2.2) |
| 4-(1) | CH$_3$(CH$_2$)$_2$OCO— | ESI-MS (m/z): 602 [(M+NH$_4$)$^+$]<br>IR (neat, cm$^{-1}$): 3402, 1747, 1697, 1609<br>NMR (DMSO-d$_6$) δ: 0.83 (3H, t, J=7.5), 1.54 (2H, m), 2.28 (3H, s), 2.92–2.99 (2H, m), 3.03–3.32 (5H, m), 3.60 (1H, m), 3.96 (2H, dt, J=1.3, 6.6), 4.11 |

TABLE 1-continued

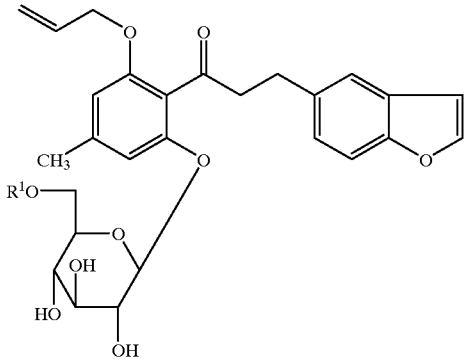

| Ex. No. | R¹ | Physicochemical properties |
|---|---|---|
| | | (1H, dd, J=7.0, 11.7), 4.37 (1H, dd, J=1.7, 11.7), 4.50 (2H, dt, J=4.9, 1.5), 4.91 (1H, d, J=7.7), 5.16 (1H, ddt, J=10.6, 1.8, 1.5), 5.21 (1H, d, J=5.1), 5.26 (1H, ddt, J=17.2, 1.8, 1.7), 5.35 (2H, m), 5.89 (1H, ddt, J=17.2, 10.6, 4.9), 6.58 (1H, s), 6.62 (1H, s), 6.87 (1H, dd, J=0.9, 2.2), 7.16 (1H, dd, J=1.8, 8.4), 7.45 (1H, d, J=8.4), 7.47 (1H, d, J=2.0), 7.93 (1H, d, J=2.2) |

TABLE 2

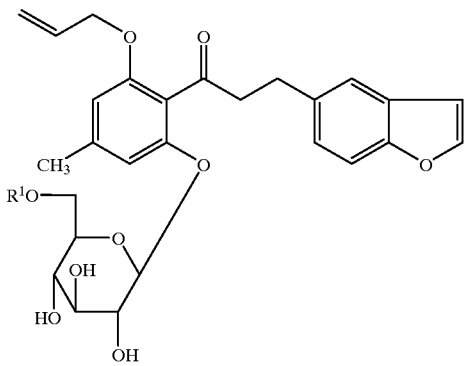

| Ex. No. | R¹ | Physicochemical properties |
|---|---|---|
| 5-(1) | ![isopropyl]—OCO— | ESI-MS (m/z): 602 [(M+NH₄)⁺]<br>IR (neat, cm⁻¹): 3400, 1743, 1698, 1609<br>NMR (DMSO-d₆) δ: 1.15, 1.17 (3H each, both d, J=6.5), 2.29 (3H, s), 2.93–2.99 (2H, m), 3.03–3.30 (5H, m), 3.60 (1H, ddd, J=2.0, 7.0, 9.0), 4.10 (1H, dd, J=7.0, 11.5), 4.35 (1H, dd, J=2.0, 11.5), 4.50 (2H, dt, J=5.0, 1.5), 4.70 (1H, heptet, J=6.5), 4.91 (1H, d, J=7.5), 5.16 (1H, ddt, J=10.5, 3.5, 1.5), 5.18 (1H, d, J=5.5), 5.26 (1H, ddt, J=17.5, 3.5, 1.5), 5.34 (2H, d, J=5.5), 5.89 (1H, ddt, J=17.0, 10.5, 5.0), 6.57 (1H, s), 6.63 (1H, s), 6.87 (1H, dd, J=1.0, 2.0), 7.16 (1H, dd, J=1.5, 8.5), 7.45 (1H, d, J=8.5), 7.47 (1H, d, J=1.5), 7.93 (IH, d, J=2.0) |
| 6-(1) | CH₃(CH₂)₃OCO— | ESI-MS (m/z): 616 [(M+NH₄)⁺]<br>IR (nujol, cm⁻¹): 3470, 3280, 1750, 1700<br>NMR (DMSO-d₆) δ: 0.84 (3H, t, J=7.3), 1.27 (2H, m), 1.51 (2H, m), 2.28 (3H, s), 2.96 (2H, m), 3.0–3.4 (5H, m), 3.60 (1H, m), 4.00 (2H, dt, J=1.0, 6.6), 4.11 (1H, dd, J=6.7, 11.6), 4.37 (1H, dd, J=1.7, 11.5), 4.50 (2H, dt, J=4.9, 1.5), 4.91 (1H, d, J=7.7), 5.16 (1H, ddt, J=10.5, 1.7, 1.5); 5.20 (1H, d, J=5.1), 5.25 (1H, ddt, J=17.3, 1.7, 1.7), 5.34 |

TABLE 2-continued

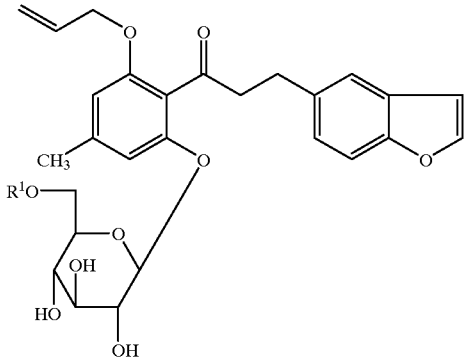

| Ex. No. | R¹ | Physicochemical properties |
|---|---|---|
| | | (1H, d, J=5.3), 5.35 (1H, d, J=5.7), 5.89 (1H, ddt, J=17.4, 10.5, 5.5), 6.58 (1H, s), 6.63 (1H, s), 6.87 (1H, dd, J=0.9, 2.2), 7.16 (1H, dd, J=1.7, 8.4), 7.45 (1H, d, J=8.5), 7.46 (1H, d, J=2.0), 7.93 (1H, d, J=2.2) |

TABLE 3

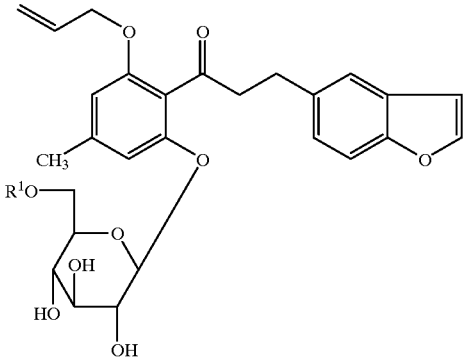

| Ex. No. | R¹ | Physicochemical properties |
|---|---|---|
| 7-(1) | CH₃CO— | FAB-MS (m/z): 541 [(M+H)⁺]<br>IR (neat, cm⁻¹): 3400, 1741, 1700<br>NMR (DMSO-d₆) δ: 1.95 (3H, s), 2.29 (3H, s), 2.95–3.02 (2H, m), 3.03–3.32 (5H, m), 3.55–3.62 (1H, m), 4.02 (1H, dd, J=7.1, 11.9), 4.32 (1H, dd, J=1.8, 11.9), 4.50 (2H, dt, J=5.0, 1.5), 4.90 (1H, d, J=7.5), 5.17 (1H, ddt, J=10.6, 1.8, 1.5), 5.20 (1H, d, J=4.9), 5.26 (1H, ddt, J=17.4, 1.8, 1.7), 5.30 (1H, d, J=5.5), 5.33 (1H, d, J=5.5), 5.90 (1H, ddt, J=17.2, 10.6, 5.0), 6.58 (1H, s), 6.62 (1H, s), 6.87 (1H, dd, J=0.9, 2.2), 7.16 (1H, dd, J=1.7, 8.4), 7.45 (1H, d, J=8.4), 7.48 (1H, d, J=1.7), 7.93 (1H, d, J=2.2) |
| 8-(1) | CH₃O〰〰OCO— | ESI-MS (m/z): 618 [(M+NH₄)⁺]<br>IR (neat, cm⁻¹): 3400, 1750, 1700<br>NMR (DMSO-d₆) δ: 2.28 (3H, s), 2.9–3.4 (7H, m), 3.22 (3H, s), 3.48 (2H, m), 3.60 (1H, m), 4.11 (1H, m), 4.13 (2H, m), 4.38 (1H, m), 4.50 (2H, dt, J=4.9, 1.6), 4.91 (1H, d, J=7.7), 5.16 (1H, m), 5.19 (1H, d, J=5.1), 5.26 (1H, m), 5.34 (1H, d, J=5.5), 5.35 (1H, d, J=5.5), 5.89 (1H, m), 6.57 (1H, s), 6.63 (1H, s), 6.87 (1H, dd, J=0.9, 2.2), 7.15 (1H, dd, J=1.8, 8.6), 7.45 (1H, d, J=8.6), 7.47 (1H, d, J=2.3), 7.93 (1H, d, J=2.2) |

TABLE 4

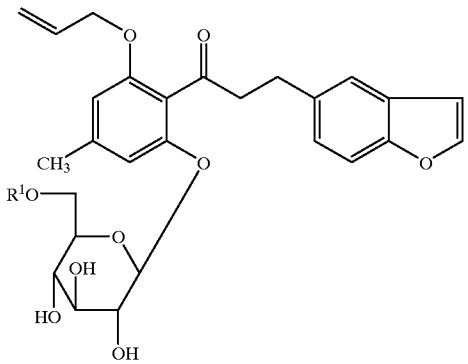

| Ex. No. | R¹ | Physicochemical properties |
|---|---|---|
| 9-(1) | CH₃OCH₂CO— | ESI-MS (m/z): 588 [(M+NH₄)⁺]<br>IR (neat, cm⁻¹): 3409, 1755, 1699, 1609<br>NMR (DMSO-d₆) δ: 2.29 (3H, s), 2.94–3.00 (2H, m), 3.03–3.34 (5H, m), 3.23 (3H, s), 3.58–3.64 (1H, m), 3.93 (1H, d, J=16.5), 4.01 (1H, d, J=16.7), 4.12 (1H, dd, J=6.9, 11.7), 4.40 (1H, dd, J=1.8, 11.7), 4.50 (2H, dt, J=4.9, 1.5), 4.93 (1H, d, J=7.5), 5.16 (1H, ddt, J=10.6, 1.8, 1.5), 5.21 (1H, d, J=5.5), 5.26 (1H, ddt, J=17.4, 1.8, 1.7), 5.33 (2H, m), 5.89 (1H, ddt, J=17.4, 10.6, 5.0), 6.58 (1H, s), 6.62 (1H, s), 6.87 (1H, dd, J=0.9, 2.2), 7.17 (1H, dd, J=1.7, 8.4), 7.45 (1H, d, J=8.4), 7.48 (1H, d, J=1.5), 7.93 (1H, d, J=2.0) |

(2) The compounds as listed in Tables 5–8 are obtained in the same manners as in Example 2-(3)

TABLE 5

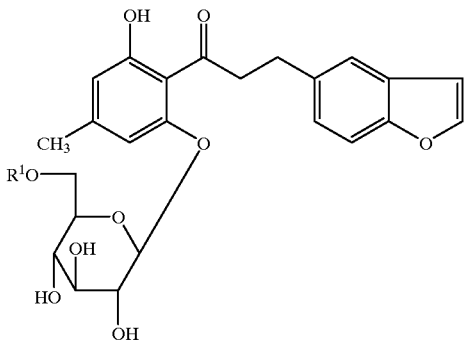

| Ex. No. | R¹ | Physicochemical properties |
|---|---|---|
| 3-(2) | CH₃CH₂OCO— | FAB-MS (m/z): 531 [(M+H)⁺]<br>IR (nujol, cm⁻¹): 3300–3500, 1733<br>NMR (DMSO-d₆) δ: 1.15 (3H, t, J=7.1), 2.24 (3H, s), 2.99 (2H, t, J=7.4), 3.14–3.42 (5H, m), 3.62–3.69 (1H, m), 4.06 (2H, q, J=7.1), 4.14 (1H, dd, J=7.0, 11.7), 4.38 (1H, dd, J=2.2, 11.7), 5.02 (1H, d, J=7.3), 5.24 (1H, d, J=4.8), 5.36 (1H, d, J=5.5), 5.38 (1H, d, J=5.3), 6.41 (1H, s), 6.51 (1H, s), 6.87 (1H, dd, J=0.9, 2.2), 7.20 (1H, dd, J=1.8, 8.4), 7.46 (1H, d, J=8.4), 7.51 (1H, d, J=1.3), 7.93 (1H, d, J=2.2), 11.8 (1H, s) |
| 4-(2) | CH₃(CH₂)₂OCO— | ESI-MS (m/z): 562 [(M+NH₄)⁺]<br>IR (neat, cm⁻¹): 3432, 1746, 1631<br>NMR (DMSO-d₆) δ: 0.83 (3H, t, J=7.4), 1.55 (2H, m), 2.24 (3H, s); 2.99 (2H, t, J=7.3), 3.16–3.33 (3H, m), 3.39 (2H, m), 3.66 (1H, m), 3.97 (2H, t, |

TABLE 5-continued

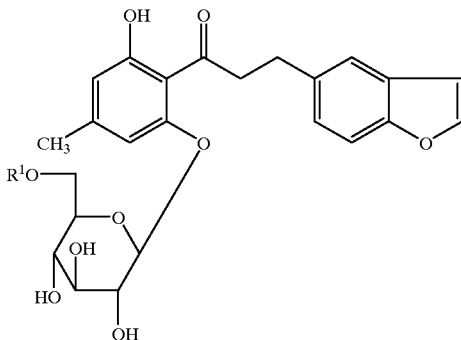

| Ex. No. | R¹ | Physicochemical properties |
|---|---|---|
| | | J=6.6), 4.14 (1H, dd, J=6.8, 11.7), 4.38 (1H, m), 5.02 (1H, d, J=7.3), 5.25 (1H, d, J=4.8), 5.37 (1H, d, J=5.3), 5.40 (1H, d, J=5.1), 6.41 (1H, s), 6.52 (1H, s), 6.87 (1H, dd, J=0.9, 2.2), 7.20 (1H, dd, J=1.7, 8.4), 7.46 (1H, d, J=8.4), 7.51 (1H, d, J=1.3), 7.93 (1H, d, J=2.2), 11.8 (1H, s) |

TABLE 6

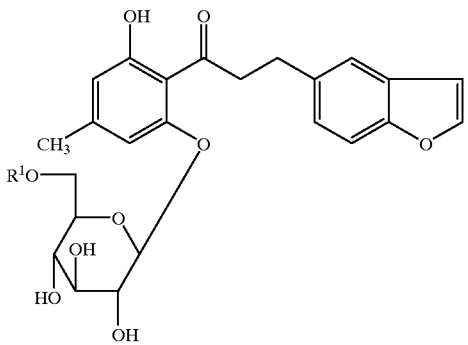

| Ex. No. | R¹ | Physicochemical properties |
|---|---|---|
| 5-(2) | (CH₃)₂CHOCO— | ESI-MS (m/z): 562 [(M+NH₄)⁺]<br>IR (nujol cm⁻¹): 3603, 3489, 3421, 1291, 1711, 1619<br>NMR (DMSO-$d_6$) δ: 1.15, 1.17 (3H each, both d, J=6.5), 2.25 (3H, s), 2.99 (2H, t, J=7.5), 3.17–3.42 (5H, m), 3.64 (1H, ddd, J=2.0, 7.0, 9.0), 4.12 (1H, dd, J=7.0, 11.5), 4.36 (1H, dd, J=2.0, 11.5), 4.71 (1H, heptet, J=6.5), 5.02 (1H, d, J=7.5), 5.24 (1H, d, J=5.0), 5.37, 5.40 (1H each, both d, J=5.5), 6.40, 6.52 (1H each, both s), 6.88 (1H, dd, J=1.0, 2.0), 7.20 (1H, dd, J=2.0, 8.5), 7.46 (1H, d, J=8.5), 7.51 (1H, d, J=2.0), 7.93 (1H, d, J=2.0), 11.80 (1H, s) |
| 6-(2) | CH₃(CH₂)₃OCO— | ESI-MS (m/z): 576 [(M+NH₄)⁺]<br>IR (nujol, cm⁻¹): 3400, 1745, 1630<br>NMR (DMSO-$d_6$) δ: 0.83 (3H, t, J=7.3), 1.27 (2H, m), 1.51 (2H, m), 2.24 (3H, s), 2.99 (2H, t, J=7.6), 3.1–3.4 (5H, m), 3.66 (1H, m), 4.02 (2H, t, J=6.6), 4.14 (1H, dd, J=6.8, 11.5), 4.38 (1H, dd, J=1.5, 11.5), 5.02 (1H, d, J=7.5), 5.24 (1H, d, J=4.9), 5.37 (1H, d, J=5.3), 5.39 (1H, d, J=5.1), 6.41 (1H, s), 6.52 (1H, s), 6.87 (IH, dd, J=1.1, 2.2), 7.20 (1H, dd, J=1.7, 8.6), 7.46 (1H, d, J=8.6), 7.51 (1H, d, J=1.3), 7.93 (1H, d, J=2.2), 11.80 (1H, s) |

TABLE 7
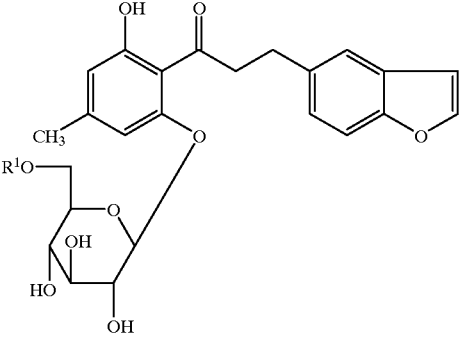
| Ex. No. | R[1] | Physicochemical properties |
|---|---|---|
| 7-(2) | CH₃CO— | m.p. 86° C. (gradually decomposed) |
| | | FAB-MS (m/z): 523 [(M+H)⁺] |
| | | IR (nujol, cm⁻¹): 3400–3500, 1738, 1713 |
| | | NMR (DMSO-d₆) δ: 1.97 (3H, s), 2.25 (3H, s), 2.99 (2H, t, J=7.7), 3.14–3.49 (5H, m), 3.63 (1H, m), 4.03 (1H, dd, J=7.1, 14.3), 4.44 (1H, m), 5.01 (1H, d, J=7.5), 5.25 (1H, d, J=4.8), 5.33 (1H, d, J=5.5), 5.39 (1H, d, J=5.1), 6.41 (1H, s), 6.51 (1H, s), 6.88 (1H, dd, J=0.9, 2.2), 7.21 (1H, dd, J=1.8, 8.4), 7.47 (1H, d, J=8.4), 7.52 (1H, d, J=1.3), 7.94 (1H, d, J=2.2), 11.7 (1H, s) |
| 8-(2) | CH₃OCH₂CH₂OCO— | ESI-MS (m/z): 578 [(M+NH₄)⁺] |
| | | IR (neat, cm⁻¹): 3430, 1750, 1630 |
| | | NMR (DMSO-d₆) δ: 2.24 (3H, s), 2.99 (2H, t, J=7.3), 3.15–3.45 (5H, m), 3.21 (3H, s), 3.48 (2H, m), 3.63 (1H, m), 4.14 (3H, m), 4.40 (1H, dd, J=1.9, 11.4), 5.02 (1H, d, J=7.3), 5.23 (1H, d, J=4.9), 5.36 (1H, d, J=5.3), 5.38 (1H, d, J=5.1), 6.41 (1H, d, J=0.7), 6.52 (1H, d, J=0.7), 6.87 (1H, dd, J=1.1, 2.2), 7.20 (1H, dd, J=1.8, 8.4), 7.46 (1H, d, J=8.4), 7.51 (1H, d, J=1.1), 7.92 (1H, d, J=2.2), 11.80 (1H, s) |

TABLE 8

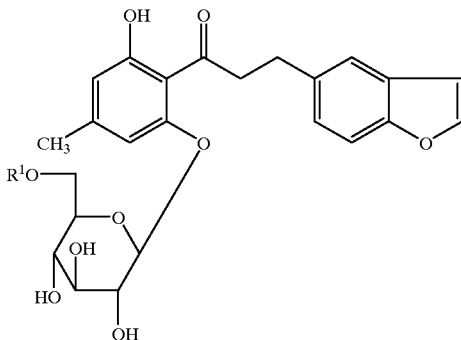

| Ex. No. | $R^1$ | Physicochemical properties |
|---|---|---|
| 9-(2) | $CH_3OCH_2CO-$ | m.p. 65–68° C.<br>ESI-MS (m/z): 548 [(M+NH$_4$)$^+$]<br>IR (nujol, cm$^{-1}$): 3475, 1751, 1630<br>NMR (DMSO-d$_6$) δ: 2.25 (3H, s), 2.99 (2H, t, J=7.5), 3.15–3.42 (5H, m), 3.24 (3H, s), 3.67 (1H, m), 3.96 (1H, d, J=16.5), 4.02 (1H, d, J=16.7), 4.14 (1H, dd, J=6.9, 11.7), 4.42 (1H, dd, J=1.7, 11.7), 5.02 (1H, d, J=7.3), 5.26 (1H, d, J=4.8), 5.36 (1H, d, J=5.5), 5.39 (1H, d, J=5.3), 6.41 (1H, s), 6.50 (1H, s), 6.88 (1H, dd, J=0.9, 2.2), 7.20 (1H, dd, J=1.7, 8.4), 7.47 (1H, d, J=8.4), 7.51 (1H, d, J=1.5), 7.94 (1H, d, J=2.2), 11.76 (1H, s) |

Example 10

3-(5-Benzo[b]furanyl)-2'-(β-D-glucopyranosyloxy)-6'-hydroxy-4'-methylpropiophenone (400 mg) is dissolved in trimethyl ortho-acetate (5 ml), and thereto is added pyridinium p-toluenesulfonate (22 mg), and the mixture is stirred at room temperature for one hour. The reaction mixture is diluted with ethyl acetate, and poured into a saturated sodium hydrogen carbonate solution. The mixture is shaken, and the organic layer is separated, washed with water, dried, and concentrated under reduced pressure. The residue is purified by silica gel column chromatography (solvent; chloroform/methanol) to give 3-(5-benzo-[b]furanyl)-2'-(4,6-O-(1-methoxyethylidene)-β-D-glucopyranosyloxy)-6'-hydroxy-4'-methylpropiophenone (320 mg).

ESI-MS (m/z): 537 [(M+Na)$^+$], 515 [(M+H)$^+$]

IR (nujol, cm$^{-1}$): 3423, 1631

NMR (DMSO-d$_6$) δ: 1.40 (3H, s), 2.25 (3H, s), 2.99 (2H, t, J=7.5), 3.23 (3H, s), 3.26–3.82 (8H, m), 5.18 (1H, d, J=7.7), 5.38 (1H, d, J=5.3), 5.61 (1H, d, J=5.7), 6.41 (1H, s), 6.55 (1H, s), 6.84 (1H, dd, J=0.9, 2.2),7.19 (1H, dd, J=1.7, 8.4), 7.47 (1H, d, J=8.4), 7.51 (1H, d, J=1.3), 7.94 (1H, d, J=2.2), 11.7 (1H, s)

Example 11

(1) 3-(5-Benzo[b]furanyl)-2'-(β-D-glucopyranosyloxy)-6'-hydroxy-4'-methylpropiophenone (1.87 g) is suspended in dichloromethane (36 ml), and thereto are added p-toluenesulfonic acid (78 mg) and benzaldehyde dimethyl acetal (930 mg) at room temperature. The mixture is stirred at room temperature for 1.5 hour. The mixture is concentrated under reduced pressure, and to the residue are added ethyl acetate and a saturated aqueous sodium hydrogen carbonate solution. The mixture is shaken, and the organic layer is separated, washed with water, dried, and concentrated under reduced pressure. The residue is purified by silica gel column chromatography (solvent; chloroform/acetone) to give 3-(5-benzo[b]furanyl)-2'-(4,6-O-benzylidene-β-D-glucopyranosyloxy)-6'-hydroxy-4'-methylpropiophenone (2.03 g).

ESI-MS (m/z): 569 [(M+Na)$^+$], 547 [(M+H)$^+$]

IR (neat, cm$^{-1}$): 3450, 1631

NMR (DMSO-d$_6$) δ: 2.09 (3H, s), 3.01 (2H, t, J=7.4), 3.34–3.48 (4H, m), 3.58–3.70 (3H, m), 4.23 (1H, m), 5.22 (1H, d, J=7.7), 5.51 (1H, d, J=4.9), 5.59 (1H, s), 5.64 (1H, d, J=5.5), 6.42 (1H, s), 6.59 (1H, s), 6.90 (1H, dd, J=0.9, 2.2), 7.22 (1H, dd, J=1.8, 8.4), 7.36–7.53 (7H, m), 7.95 (1H, d, J=2.2),11.80 (1H, s)

(2) 3-(5-Benzo[b]furanyl)-2'-(4,6-O-benzylidene-β-D-glucopyranosyloxy)-6'-hydroxy-4'-methylpropiophenone (1.00 g) is dissolved in N,N-dimethylformamide (10 ml), and thereto are added imidazole (747 mg) and t-butyldimethylchlorosilane (827 mg). The mixture is stirred at room temperature for 13 hours, and poured into ice-water. The mixture is extracted with ethyl acetate, and the organic layer is washed with water, dried, and concentrated under reduced pressure. The residue is purified by silica gel column chromatography (solvent; hexane/ethyl acetate) to give 3-(5-benzo[b]furanyl)-2'-(3-O-t-butyldimethylsilyl-4,6-O-benzylidene-β-D-glucopyranosyloxy)-6'-t-butyldimethylsilyloxy-4'-methylpropiophenone (1.06 g).

FAB-MS (m/z): 797 [(M+Na)$^+$]

IR (nujol, cm$^{-1}$): 3459, 1691, 1610

NMR (DMSO-d$_6$) δ: 0.01 (3H, s), 0.08 (3H, s), 0.18 (6H, s), 0.86 (9H, s), 0.89 (9H, s), 2.28 (3H, s), 2.93–3.02 (2H, m), 3.04–3.15 (2H, m), 3.28 (1H, m), 3.44 (1H, m), 3.62 (2H, m), 3.74 (1H, t, J=8.8), 4.18 (1H, m), 5.18 (1H, d, J=7.9), 5.56 (1H, d, J=7.0), 5.58 (1H, s), 6.40 (1H, s), 6.71 (1H, s), 6.88 (1H, dd, J=0.9, 2.2), 7.17 (1H, dd, J=1.8, 8.6), 7.36–7.49 (7H, m), 7.93 (1H, d, J=2.2)

(3) 3-(5-Benzo[b]furanyl)-2'-(3-O-t-butyldimethylsilyl-4,6-O-benzylidene-β-D-glucopyranosyloxy)-6'-t- butyldimethylsilyloxy-4'-methylpropiophenone (1.04 g) is dissolved in pyridine (5.4 ml), and thereto is added acetic anhydride (2.7 ml). The mixture is stirred at room temperature overnight, and poured into chilled 10% aqueous citric acid solution. The mixture is extracted with ethyl acetate, and the organic layer is washed with water and a saturated aqueous sodium hydrogen carbonate solution, dried, and concentrated under reduced pressure to give 3-(5-benzo[b]furanyl)-2'-(2-O-acetyl-3-O-t-butyldimethylsilyl-4,6-O-benzylidene-β-D-glucopyranosyloxy)-6'-t-butyldimethylsilyloxy-4'-methylpropiophenone (1.09 g).

ESI-MS (m/z): 840 [(M+Na)$^+$]

IR (neat, cm$^{-1}$): 1753, 1705, 1609

NMR (DMSO-d$_6$) δ:−0.04 (3H, s), 0.00 (3H, s), 0.17 (3H, s), 0.17 (3H, s), 0.78 (9H, s), 0.86 (9H, s), 2.02 (3H, s), 2.28 (3H, s), 2.80–3.02 (4H, m), 3.62 (1H, t, J=9.0), 3.70–3.85 (2H, m), 4.04 (1H, t, J=9.2), 4.29 (1H, dd, J=3.7, 8.8), 4.93 (1H, t, J=9.0), 5.38 (1H, d, J=8.1), 5.65 (1H, s), 6.42 (1H, s), 6.65 (1H, s), 6.90 (1H, dd, J=0.9, 2.2), 7.15 (1H, dd, J=1.8, 8.6), 7.37–7.47 (6H, m), 7.50 (1H, d, J=8.6), 7.94 (1H, J=2.2)

(4) 3-(5-Benzo[b]furanyl)-2'-(2-O-acetyl-3-O-t-butyldimethylsilyl-4,6-O-benzylidene-β-D-glucopyranosyloxy)-6'-t-butyldimethylsilyloxy-4'-methylpropiophenone (1.07 g) is dissolved in a mixture of tetrahydrofuran (23 ml) and acetic acid (2.3 ml), and thereto is added tetra-n-butylammonium fluoride (685 mg), and the mixture is stirred at room temperature for 25 minutes. The reaction mixture is concentrated, and the residue is dissolved in ethyl acetate, and poured into ice-water. The organic layer is washed with water, dried, and concentrated under reduced pressure to give 3-(5-benzo[b]furanyl)-2'-(2-O-acetyl-3-O-t-butyldimethylsilyl-4,6-O-benzylidene-β-D-glucopyranosyloxy)-6'-hydroxy-4'-methylpropiophenone (968 mg).

FAB-MS (m/z): 725 [(M+Na)$^+$]

IR (neat, cm$^{-1}$): 1753, 1634

NMR (DMSO-d$_6$) δ: −0.05 (3H, s), 0.00 (3H, s), 0.78 (9H, s), 2.03 (3H, s), 2.24 (3H, s), 2.92–2.99 (2H, m), 3.05–3.11 (2H, m), 3.60 (1H, t, J=9.1), 3.72 (1H, t, J=9.3), 3.77–3.85 (1H, m), 4.04 (1H, m), 4.27 (1H, dd, J=4.2, 9.2), 4.95 (1H, t, J=8.5), 5.46 (1H, d, J=8.1), 5.64 (1H, s), 6.42 (1H, s), 6.52 (1H, s), 6.89 (1H, dd, J=0.9, 2.2), 7.20 (1H, dd, J=1.7, 8.3), 7.36–7.46 (5H, m), 7.50 (1H, d, J=8.3), 7.51 (1H, m), 7.94 (1H, d, J=2.2), 10.7 (1H, s)

(5) 3-(5-Benzo[b]furanyl)-2'-(2-O-acetyl-3-O-t-butyldimethylsilyl-4,6-O-benzylidene-β-D-glucopyranosyloxy)-6'-hydroxy-4'-methylpropiophenone (958 mg) is dissolved in acetic acid (35 ml), and thereto are added water (4 ml) and p-toluenesulfonic acid (75 mg), and the mixture is stirred at room temperature for four days. The reaction mixture is poured into ice-water (700 ml), and the mixture is extracted with ethyl acetate. The organic layer is washed with water, dried, and concentrated under reduced pressure. The residue is purified by silica gel column chromatography (solvent; chloroform/methanol) to give 3-(5-benzo[b]furanyl)-2'-(2-O-acetyl-β-D-glucopyranosyloxy)-6'-hydroxy-4'-methylpropiophenone (420 mg).

M.p. 160° C.~(gradually melting)

ESI-MS (m/z): 518 [(M+NH$_4$)$^+$]

IR (nujol, cm$^{-1}$): 3100–3510, 1752

NMR (DMSO-d$_6$) δ: 1.99 (3H, s), 2.22 (3H, s), 2.90–2.97 (2H, m), 3.03–3.11 (2H, m), 3.21–3.31 (1H, m), 3.42–3.53 (3H, m), 3.72 (1H, m), 4.67 (1H, t, J=5.6), 4.78 (1H, dd, J=8.2, 9.5), 5.20 (1H, d, J=8.1), 5.28 (1H, d, J=5.3), 5.36 (1H, d, J=5.5), 6.39 (1H, s), 6.52 (1H, s), 6.88 (1H, dd, J=0.9, 2.2), 7.18 (1H, dd, J=1.7, 8.4), 7.47 (1H, d, J=8.4), 7.50 (1H, d, J=1.3), 7.93 (1H, d, J=2.2), 10.86 (1H, s)

Example 12

(1) 3-(5-Benzo[b]furanyl)-2'-(4,6-O-benzylidene-β-D-glucopyranosyloxy)-6'-hydroxy-4'-methylpropiophenone (2.02 g) is dissolved in pyridine (20 ml), and thereto is added acetic anhydride (2.27 g). The mixture is stirred at room temperature for 4.5 hours, and poured into chilled 10% aqueous citric acid solution, and the mixture is extracted with ethyl acetate. The organic layer is washed with water, dried, and concentrated under reduced pressure to give 3-(5-benzo[b]furanyl)-2'-(2,3-di-O-acetyl-4,6-O-benzylidene-β-D-glucopyranosyloxy)-6'-acetoxy-4'-methylpropiophenone (2.37 g).

M.p. 200–203° C.

ESI-MS (m/z): 690 [(M+NH$_4$)$^+$]

IR (nujol, cm$^{-1}$): 1764, 1747, 1699, 1619

NMR (DMSO-d$_6$) δ: 1.94 (3H, s), 2.01 (3H, s), 2.02 (3H, s), 2.34 (3H, s), 2.87–3.03 (4H, m), 3.76 (1H, t, J=9.9), 3.90 (1H, t, J=9.4), 3.97 (1H, dd, J=4.5, 9.9), 4.44 (1H, dd, J=4.6, 10.0), 5.07 (1H, dd, J=7.9, 8.1), 5.40 (1H, t, J=9.4), 5.63 (1H, s), 5.68 (1H, d, J=7.9), 6.74 (1H, s), 6.91 (1H, dd, J=0.9, 2.2), 7.00 (1H, s), 7.17 (1H, dd, J=1.8, 8.6), 7.39 (5H, s), 7.49 (1H, d, J=1.3), 7.51 (1H, d, J=8.4), 7.95 (1H, d, J=2.2)

(2) 3-(5-Benzo[b]furanyl)-2'-(2,3-di-O-acetyl-4,6-O-benzylidene-β-D-glucopyranosyloxy)-6'-acetoxy-4'-methylpropiophenone (2.04 g) is suspended in acetic acid (60 ml), and thereto are added water (6 ml) and p-toluenesulfonic acid (58 mg). The mixture is stirred at room temperature for 20 hours, and poured into ice-water (800 ml). The mixture is allowed to stand for one hour, and the precipitated insoluble resinous material is separated by filtration, and dissolved in ethyl acetate. The organic layer is washed with a saturated aqueous sodium hydrogen carbonate solution, dried, and concentrated under reduced pressure. The residue is purified by silica gel column chromatography (solvent; chloroform/methanol) to give 3-(5-benzo[b]furanyl)-2'-(2,3-di-O-acetyl-β-D-glucopyranosyloxy)-6'-acetoxy-4'-methylpropiophenone (1.72 g).

ESI-MS (m/z): 602 [(M+NH$_4$)$^+$]

IR (nujol, cm$^{-1}$): 3404,1751

NMR (DMSO-d$_6$) δ: 1.87 (3H, s), 2.00 (3H, s), 2.00 (2H, s), 2.31 (3H, s), 2.84–3.11 (4H, m), 3.48–3.57 (2H, m), 3.64–3.77 (2H, m), 4.77 (1H, t, J=5.8), 4.89 (1H, dd, J=8.1, 9.7), 5.10 (1H, t, J=9.7), 5.50 (1H, d, J=8.1), 5.59 (1H, d, J=5.7), 6.70 (1H, s), 6.89 (1H, dd, J=0.9, 2.2), 7.00 (1H, s), 7.16 (1H, dd, J=1.5, 8.5), 7.47–7.50 (2H, m), 7.94 (1H, d, J=2.2)

Example 13

(1) 3-(5-Benzo[b]furanyl)-2'-(2,3-di-O-acetyl-4,6-O-benzylidene-β-D-glucopyranosyloxy)-6'-acetoxy-4'-methylpropiophenone (671 mg) is dissolved in a mixture of tetrahydrofuran (5 ml), methanol (5 ml) and water (0.1 ml), and thereto is added sodium hydrogen carbonate (419 mg). The mixture is stirred at room temperature for 30 hours, and poured into water. The mixture is extracted with ethyl acetate, and the organic layer is washed with water, dried, and concentrated under reduced pressure. The residue is purified by silica gel column chromatography (solvent; hexane/ethyl acetate) to give 3-(5-benzo[b]-furanyl)-2'-(2,3-di-O-acetyl-4,6-O-benzylidene-β-D-glucopyranosyloxy)-6'-hydroxy-4'-methylpropiophenone (410 mg).

M.p. 187–189° C.

ESI-MS (m/z): 648 [(M+NH$_4$)$^+$]

IR (neat, cm$^{-1}$): 1754, 1633

NMR (DMSO-d$_6$) δ: 1.97 (3H, s), 2.01 (3H, s), 2.25 (3H, s), 2.90–2.98 (2H, m), 3.01–3.09 (2H, m), 3.76 (1H, t, J=9.9), 3.88 (1H, t, J=9.4), 3.95 (1H, dd, J=4.6, 9.5), 4.32 (1H, dd, J=4.6, 10.1), 5.05 (1H, dd, J=7.9, 9.3), 5.40 (1H, t, J=9.3), 5.63 (1H, s), 5.63 (1H, d, J=7.9), 6.43 (1H, s), 6.53 (1H, s), 6.90 (1H, dd, J=0.9, 2.2), 7.19 (1H, dd, J=1.7, 8.6), 7.39 (5H, s), 7.50 (2H, m), 7.95 (1H, d, J=2.2), 10.70 (1H, s)

(2) 3-(5-Benzo[b]furanyl)-2'-(2,3-di-O-acetyl-4,6-O-benzylidene-β-D-glucopyranosyloxy)-6'-hydroxy-4'-methylpropiophenone (395 mg) is dissolved in acetic acid (14 ml), and thereto are added water (1.4 ml) and p-toluenesulfonic acid (12 mg). The mixture is stirred at room temperature for two days, poured into ice-water, and allowed to stand for one hour. The colorless precipitates are collected by filtration, and dissolved in ethyl acetate. The mixture is washed with water, dried, and concentrated under reduced pressure to remove the solvent. The residue is purified by silica gel column chromatography (solvent; chloroform/methanol) to give 3-(5-benzo[b]furanyl)-2'-(2,3-di-O-acetyl-β-D-glucopyranosyloxy)-6'-hydroxy-4'-methylpropiophenone (297 mg).

M.p. 151–153° C.

ESI-MS (m/z): 560 [(M+NH$_4$)$^+$]

IR (nujol, cm$^{-1}$): 3543, 3288, 1751, 1729

NMR (DMSO-d$_6$) δ: 1.91 (3H, s), 1.99 (3H, s), 2.23 (3H, s), 2.89–2.96 (2H, m), 3.02–3.09 (2H, m), 3.46–3.80 (4H, m), 4.75 (1H, t, J=5.7), 4.88 (1H, dd, J=8.0, 9.8), 5.09 (1H, t, J=9.4), 5.43 (1H, d, J=8.0), 5.58 (1H, d, J=5.7), 6.41 (1H, s), 6.54 (1H, s), 6.88 (1H, dd, J=0.9, 2.2), 7.17 (1H, dd, J=1.8, 8.4), 7.47 (1H, d, J=8.9), 7.49 (1H, s), 7.94 (1H, d, J=2.2), 10.48 (1H, s)

Example 14

(1) 3-(5-Benzo[b]furanyl)-2'-(4,6-O-benzylidene-β-D-glucopyranosyloxy)-6'-hydroxy-4'-methylpropiophenone (600 mg) is dissolved in N,N-dimethylacetamide (4 ml), and thereto is added triethylamine (123 mg). To the mixture is added dropwise a solution of methyl chloroformate (115 mg) in N,N-dimethylacetamide (2 ml) under ice-cooling over a period of 40 minutes. The mixture is stirred at the same temperature for 10 minutes, and poured into chilled 10% aqueous citric acid solution, and extracted with ethyl acetate. The organic layer is washed with water, dried, and concentrated under reduced pressure. The residue is purified by silica gel column chromatography (solvent; chloroform/methanol) to give 3-(5-benzo[b]furanyl)-2'-(4,6-O-benzylidene-β-D-glucopyranosyloxy)-6'-methoxycarbonyloxy-4'-methylpropiophenone (637 mg).

ESI-MS (m/z): 622 [(M+NH$_4$)$^+$]

IR (nujol, cm$^{-1}$): 3383, 1762, 1689, 1618

NMR (DMSO-d$_6$) δ: 2.34 (3H, s), 2.92–2.98 (2H, m), 3.05–3.25 (2H, m), 3.33–3.47 (2H, m), 3.54–3.70 (3H, m), 3.75 (3H, s), 4.22 (1H, m), 5.28 (1H, d, J=7.9), 5.51 (1H, d, J=5.3), 5.57 (1H, s), 5.68 (1H, d, J=5.9), 6.81 (1H, s), 6.91 (1H, dd, J=0.9, 2.2), 7.09 (1H, s), 7.19 (1H, dd, J=1.7, 8.6), 7.37–7.48 (5H, m), 7.50 (1H, d, J=8.6), 7.50 (1H, d, J=1.7), 7.95 (1H, d, J=2.2)

(2) 3-(5-Benzo[b]furanyl)-2'-(4,6-O-benzylidene-β-D-glucopyranosyloxy)-6'-methoxycarbonyloxy-4'-methylpropiophenone (618 mg) is dissolved in acetic acid (60 ml), and thereto are added water (1.4 ml) and p-toluenesulfonic acid (19 mg), and the mixture is stirred at room temperature overnight. The reaction mixture is poured into ice-water, and extracted with ethyl acetate. The organic layer is washed with a saturated aqueous sodium hydrogen carbonate solution, dried, and concentrated under reduced pressure. The residue is purified by silica gel column chromatography (solvent; chloroform/methanol) to give 3-(5-benzo[b]furanyl)-2'-(β-D-glucopyranosyloxy)-6'-methoxycarbonyloxy-4'-methylpropiophenone (428 mg).

ESI-MS (m/z): 534 [(M+NH$_4$)$^+$]

IR (neat, cm$^{-1}$): 3387, 1765

NMR (DMSO-d$_6$) δ: 2.32 (3H, s), 2.90–2.98 (2H, m), 3.09–3.50 (7H, m), 3.67–3.74 (1H, m), 3.74 (3H, s), 4.60 (1H, t, J=5.7), 5.04 (1H, d, J=7.5), 5.08 (1H, d, J=5.3), 5.15 (1H, d, J=4.9), 5.37 (1H, d, J=5.5), 6.78 (1H, m), 6.88 (1H, dd, J=0.9, 2.2), 7.03 (1H, s), 7.19 (1H, dd, J=1.8, 8.4), 7.46 (1H, d, J=8.4), 7.51 (1H, d, J=1.3), 7.93 (1H, d, J=2.2)

Example 15

(1) The corresponding starting compounds are treated in the same manner as in Example 14-(1) to give 3-(5-benzo[b]furanyl)-2'-(4,6-O-benzylidene-β-D-glucopyranosyloxy)-6'-acetoxy-4'-methylpropiophenone.

ESI-MS (m/z): 606 [(M+NH$_4$)$^+$]

IR (nujol, cm$^{-1}$): 3367, 1767, 1690, 1617

NMR (DMSO-d$_6$) δ: 2.03 (3H, s), 2.33 (3H, s), 2.92–3.00 (2H, m), 3.05–3.73 (7H, m), 4.17–4.27 (1H, m), 5.26 (1H, d, J=7.7), 5.50 (1H, d, J=5.3), 5.58 (1H, s), 5.68 (1H, d, J=5.9), 6.68 (1H, m), 6.91 (1H, dd, J=0.9, 2.2), 7.05 (1H, s), 7.19 (1H, dd, J=1.6, 8.6), 7.37–7.52 (7H, m), 7.95 (1H, d, J=2.2)

(2) 3-(5-Benzo[b]furanyl)-2'-(4,6-O-benzylidene-β-D-glucopyranosyloxy)-6'-acetoxy-4'-methylpropiophenone is treated in the same manner as in Example 14-(2) to give 3-(5-benzo[b]furanyl)-2'-(β-D-glucopyranosyloxy)-6'-acetoxy-4'-methylpropiophenone.

ESI-MS (m/z): 518 [(M+NH$_4$)$^+$]

IR (neat, cm$^{-1}$): 3393, 1769, 1691, 1618, 1198

NMR (DMSO-d$_6$) δ: 2.02 (3H, s), 2.30 (3H, s), 2.89–3.02 (2H, m), 3.06–3.51 (7H, m), 3.67–3.75 (1H, m), 4.58 (1H, t, J=5.7), 5.02 (1H, d, J=7.3), 5.05 (1H, d, J=5.1), 5.12 (1H, d, J=4.8), 5.34 (1H, d, J=5.5), 6.64 (1H, s), 6.88 (1H, dd, J=0.9, 2.2), 6.99 (1H, s), 7.19 (1H, dd, J=1.7, 8.4), 7.47 (1H, d, J=8.4), 7.51 (1H, d, J=1.3), 7.93 (1H, d, J=2.0)

Example 16

3-(5-Benzo[b]furanyl)-2'-(β-D-glucopyranosyloxy)-6'-hydroxy-4'-methylpropiophenone (500 mg) is dissolved in N,N-dimethylacetamide (3.5 ml), and thereto is added triethylamine (315 mg). To the mixture is added dropwise acetyl chloride (282 mg) under ice-cooling, and the mixture is stirred under ice-cooling for 30 minutes, and stirred at room temperature overnight. The reaction mixture is poured into chilled 10% aqueous citric acid solution, and extracted with ethyl acetate. The organic layer is washed with water, dried, and concentrated under reduced pressure. The residue is purified by silica gel column chromatography (solvent; chloroform/methanol) to give 3-(5-benzo[b]-furanyl)-2'-(6-O-acetyl-β-D-glucopyranosyloxy)-6'-acetoxy-4'-methylpropiophenone (304 mg).

ESI-MS (m/z): 560 [(M+NH$_4$)$^+$]

IR (neat, cm$^{-1}$): 3417, 1769, 1740, 1695, 1618

NMR (DMSO-d$_6$) δ: 1.97 (3H, s), 2.02 (3H, s), 2.31 (3H, s), 2.88–2.98 (2H, m), 3.04–3.32 (5H, m), 3.62–3.70 (1H, m), 4.03 (1H, dd, J=7.2, 14.1), 4.35 (1H, dd, J=1.8, 11.7), 5.04 (1H, d, J=7.5), 5.25 (1H, d, J=4.9), 5.34 (1H, d, J=5.3), 5.44 (1H, d, J=5.5), 6.67 (1H, s), 6.88 (1H, dd, J=0.9, 2.2),6.95 (1H, s), 7.18 (1H, dd, J=1.8, 8.4), 7.47 (1H, d, J=8.4), 7.50 (1H, d, J=1.5),7.94 (1H, d, J=2.2)

Example 17

(1) 3-(5-Benzo[b]furanyl)-2'-(β-D-glucopyranosyloxy)-6'-hydroxy-4'-methylpropiophenone (3.0 g) is dissolved in 2,4,6-collidine (33 ml). The mixture is cooled to 40° C. with dry ice-acetone and thereto is added dropwise with stirring a solution of 4-nitrophenyl chloroformate (1.71 g) in dichloromethane (8.6 ml). The mixture is stirred at 40° C. for 1.5 hour, and stirred at room temperature for one hour, and further stirred at 53° C. for three hours. After cooling, the reaction mixture is poured into a chilled 10% hydrochloric acid, and the mixture is extracted with ethyl acetate. The organic layer is washed with water, dried, and concentrated under reduced pressure. The residue is purified by silica gel column chromatography (solvent; chloroform/acetone) to give 3-(5-benzo[b]furanyl)-2'-(4,6-O-carbonyl-β-D-glucopyranosyloxy)-6'-hydroxy-4'-methylpropiophenone (2.16 g).

FAB-MS (m/z): 507 [(M+Na)$^+$], 485 [(M+H)$^+$]

IR (nujol, cm$^{-1}$): 3386, 1753, 1630

NMR (DMSO-d$_6$) δ: 2.25 (3H, s), 2.99 (2H, t, J=7.4), 3.30–3.40 (3H, m), 3.64 (1H, m), 4.09–4.21 (2H, m), 4.26 (1H, dd, J=9.3, 9.7), 4.49 (1H, dd, J=5.3, J=9.2), 5.26 (1H, d, J=7.9), 5.80 (1H, d, J=5.9), 5.86 (1H, d, J=5.7), 6.43 (1H, s), 6.55 (1H, s), 6.89 (1H, dd, J=0.9, 2.2), 7.19 (1H, dd, J=1.8, 8.6), 7.49 (1H, d, J=8.6), 7.50 (1H, d, J=1.9), 7.94 (1H, d, J=2.2), 11.6 (1H, s)

(2) 3-(5-Benzo[b]furanyl)-2'-(4,6-O-carbonyl-β-D-glucopyranosyloxy)-6'-hydroxy-4'-methylpropiophenone (2.13 g) is dissolved in methanol (40 ml), and thereto is added p-toluenesulfonic acid (84 mg), and the mixture is stirred at room temperature for one hour. The reaction mixture is diluted with ethyl acetate, and poured into a saturated sodium hydrogen carbonate solution. The mixture is shaken, and the organic layer is separated, washed with water, dried, and concentrated under reduced pressure. The residue is purified by silica gel column chromatography (solvent; chloroform/acetone) to give 3-(5-benzo[b]furanyl)-2'-(4-O-methoxycarbonyl-β-D-glucopyranosyloxy)-6'-hydroxy-4'-methylpropiophenone (986 mg).

ESI-MS (m/z): 534 [(M+NH$_4$)$^+$]

IR (neat, cm$^{-1}$): 3459, 1752, 1631

NMR (DMSO-d$_6$) δ: 2.24 (3H, s), 3.00 (2H, t, J=7.4), 3.32–3.45 (4H, m), 3.49–3.60 (2H, m), 3.66–3.73 (1H, m), 3.73 (3H,s), 4.54 (1H, t, J=9.6),4.82 (1H, t, J=5.6), 5.12 (1H, d, J=7.7), 5.52 (1H, d, J=5.7), 5.60 (1H, d, J=5.7), 6.44 (1H, d, J=0.6), 6.56 (1H, d, J=0.9), 6.90 (1H, dd, J=0.9, 2.2),7.22 (1H, dd, J=1.7, 8.4), 7.47 (1H, d, J=8.4), 7.54 (1H, d, J=1.3), 7.93 (1H, d, J=2.2), 11.8 (1H, s)

Example 18

To a solution of 3-(5-benzo[b]furanyl)-2'-(β-D-glucopyranosyloxy)-6'-hydroxy-4'-methylpropiophenone (10 g) in 2,4,6-collidine (100 ml) is added dropwise methyl chloroformate (10.31 g) at 0° C., and the mixture is stirred at 0° C. for 23 hours. The reaction mixture is poured into ice-10% hydrochloric acid (300 ml—300 ml), and the mixture is extracted with ethyl acetate (350 ml). The organic layer is washed with water, a saturated sodium hydrogen carbonate solution, and a saturated sodium chloride solution, dried, and concentrated under reduced pressure. The residue (11.96 g) is dissolved in tetrahydrofuran (200 ml), and thereto is added t-butyl amine (20 ml), and the mixture is stirred at room temperature for four hours. The reaction mixture is poured into ice-10% hydrochloric acid (150 ml—150 ml), and extracted with ethyl acetate (250 ml). The organic layer is washed with water, a saturated aqueous sodium hydrogen carbonate solution, and a saturated sodium chloride solution, dried, and concentrated under reduced pressure. The reside is recrystallized twice from water-diethyl ether-diisopropyl ether to give 3-(5-benzo[b]furanyl)-2'-(6-O-methoxycarbonyl-β-D-glucopyranosyloxy)-6'-hydroxy-4'-methylpropiophenone (9.14 g).

M.p. 78–82° C.

ESI-MS (m/z): 534 [(M+NH$_4$)$^+$]

IR (nujol, cm$^{-1}$): 3509, 3401, 3172, 1733, 1669, 1632, 1611

The data of NMR (DMSO-d$_6$) are the same as those of the compound obtained in Example 2-(3).

Example 19

3-(5-Benzo[b]furanyl)-2'-(β-D-glucopyranosyloxy)-6'-hydroxy-4'-methylpropiophenone (10 g) is dissolved in ethyleneglycol dimethyl ether (30 ml), and thereto are added dimethyl carbonate (100 ml), Novozyme 435 (2 g, manufactured by Novo Nordisk A/S, Denmark) and molecular sieves 4A powder (8 g), and the mixture is stirred at 40° C. for 24 hours, and stirred at room temperature for 14 hours. The reaction mixture is diluted with chloroform, and the insoluble materials are removed by filtration. The filtrate is concentrated to dryness, and the residue is dissolved in ethyl acetate. The mixture is washed successively with 10% aqueous hydrochloric acid, water, a saturated aqueous sodium hydrogen carbonate solution, and a saturated aqueous sodium chloride solution, dried, and concentrated under reduced pressure. The residue is recrystallized three times from ether-isopropyl ether-water to give 3-(5-benzo[b]-furanyl)-2'-(6-O-methoxycarbonyl-β-D-glucopyranosyloxy)-6'-hydroxy-4'-methylpropiophenone (7.9 g). The physicochemical properties of the compound are the same as those of the compound obtained in Example 18.

Example 20

The corresponding starting compounds are treated in the same manner as in Example 1 to give 3-(5-benzo[b]furanyl)-2'-(β-D-glucopyranosyloxy)-6'-hydroxy -4'-ethylpropiophenone.

M.p. 146–148.5° C.

ESI-MS (m/z): 490 [(M+NH$_4$)$^+$]

IR (nujol, cm$^{-1}$): 3600–3200, 1633, 1605

NMR (DMSO-d$_6$) δ: 1.15 (3H, t, J=7.5), 2.55 (2H, q, J=7.5), 3.00 (2H, t, J=7.5), 3.10–3.50 (7H, m), 3.68–3.74 (1H, m), 4.61 (1H, t, J=5.5),4.98 (1H, d, J=7.5), 5.06 (1H, d, J=5.5), 5.14 (1H, d, J=5.0), 5.31 (1H, d, J=5.5), 6.42 (1H, d, J=1.5), 6.57 (1H, d, J=1.5), 6.88 (1H, dd, J=1.0, 2.0), 7.22 (1H, dd, J=2.0, 8.5), 7.46 (1H, d, J=8.5), 7.53 (1H, d, J=2.0), 7.93 (1H, d, J=2.0), 11.90 (1H, s)

Example 21

2'-(2,3,4,6-Tetra-O-acetyl-β-D-glucopyranosyloxy)-6'-hydroxy-4'-methylacetophenone (100 g) is dissolved in a mixture of chilled ethanol (800 ml) and 50% aqueous potassium hydroxide solution (200 g), and thereto is added 5-formylbenzo[b]furan (30.91 g). The mixture is stirred at room temperature overnight under argon atmosphere. To the reaction mixture are added N,N-dimethylacetamide (400 ml), anhydrous piperazine (17.35 g) and 10% palladium-carbon (51.4% aqueous, 9.4 g), and the mixture is stirred at room temperature for two hours under atmospheric pressure of hydrogen gas. The catalyst is removed by filtration, and the filtrate is washed with diisopropyl ether, and acidified with 18% hydrochloric acid under ice-cooling. The mixture is extracted with ethyl acetate, and the organic layer is washed successively with water, a saturated aqueous sodium hydrogen carbonate solution, and a saturated aqueous sodium chloride solution, dried, and concentrated under reduced pressure. The residue is crystallized twice from water-acetonitrile to give colorless crystals (66.86 g), which is combined with the compound (137.6 g) prepared by the same procedure. The combined product (204.46 g) is recrystallized from water-ethanol to give 3-(5-benzo[b]furanyl)-2'-(β-D-glucopyranosyloxy)-6'-hydroxy-4'-methylpropiophenone (195.70 g). The physicochemical properties of the compound are the same as those of the compound obtained in Example 1.

Example 22

(1) 3-(5-Benzo[b]furanyl)-2'-(β-D-glucopyranosyloxy)-6'-allyloxy-4'-methylpropiophenone (300 mg) obtained in Example 2 is dissolved in tetrahydrofuran (3 ml), and thereto are added 2,4,6-collidine (315 mg) and diphenyl chlorophosphate (486 mg) under ice-cooling. The mixture is stirred at room temperature for 22 hours under argon atmosphere. The reaction mixture is poured into chilled 10% aqueous citric acid solution, and extracted with ethyl acetate. The organic layer is washed successively with water, a saturated aqueous sodium hydrogen carbonate solution, and a saturated aqueous sodium chloride solution, dried, and concentrated under reduced pressure. The residue is purified by silica gel column chromatography (solvent; chloroform/methanol) to give 3-(5-benzo[b]furanyl)-2'-(6-O-diphenylphosphono-β-D-glucopyranosyloxy)-6'-allyloxy-4'-methylpropiophenone (327 mg).

ESI-MS (m/z): 748 [(M+NH$_4$)$^+$]

IR (nujol, cm$^{-1}$): 3396, 1698, 1609

NMR (DMSO-d$_6$) δ: 2.17 (3H, s), 2.95 (2H, t, J=7.5), 3.0–3.3 (5H, m), 3.72 (1H, dt, J=9.5, 2.5), 4.30 (1H, ddd, J=5.5, 7.5, 11.5), 4.52 (2H, dt, J=1.5, 5.0), 4.57 (1H, ddd, J=3.5, 5.5, 11.5), 5.00 (1H, d, J=7.5), 5.16 (1H, ddt, J=11.0, 3.5, 1.5), 5.26 (1H, ddt, J=17.5, 3.5, 1.5), 5.3–5.4 (3H, br), 5.89 (1H, ddt, J=17.5, 11.0, 5.0), 6.55 (1H, s), 6.68 (1H, s), 6.86 (1H, dd, J=1.0, 2.0), 7.1–7.2 (7H, m), 7.30 (4H, dt, J=8.0, 1.5), 7.44 (1H, d, J=9.5), 7.45 (1H, d, J=2.0), 7.92 (1H, d, J=2.0)

(2) 3-(5-Benzo[b]furanyl)-2'-(6-O-diphenylphosphono-β-D-glucopyranosyloxy)-6'-allyloxy-4'-methylpropiophenone (308 mg) obtained in the above (1) is dissolved in acetonitrile (3 ml), and thereto are added ammonium formate (80 mg) and dichlorobis(triphenylphosphine)palladium (II) (3 mg), and the mixture is refluxed for 1.5 hour under argon atmosphere. The reaction mixture is cooled to room temperature, poured into ice-water, and extracted with ethyl acetate. The organic layer is washed successively with water and a saturate aqueous sodium chloride solution, dried, and concentrated under reduced pressure. The residue is purified by silica gel column chromatography (solvent; chloroform/methanol) to give 3-(5-benzo[b]furanyl)-2'-(6-O-diphenylphosphono-β-D-glucopyranosyloxy)-6'-hydroxy-4'-methylpropiophenone (246 mg).

ESI-MS (m/z): 708 [(M+NH$_4$)$^+$]

IR (nujol, cm$^{-1}$): 3405, 1630, 1600

NMR (DMSO-d$_6$) δ: 2.13 (3H, s), 2.98 (2H, t, J=7.0), 3.2–3.5 (5H, m), 3.75–3.85 (1H, m), 4.3–4.4 (1H, m), 4.55 (1H, ddd, J=3.5,5.5, 11.5), 5.10 (1H, d, J=8.0), 5.29 (1H, d, J=5.0), 5.41 (1H, d, J=4.5), 5.43 (1H, d, J=5.5), 6.39 (1H, d, J=1.0), 6.57 (1H, d, J=1.0), 6.85 (1H, dd, J=1.0, 2.0), 7.1–7.2 (7H, m), 7.29 (4H, dt, J=8.0, 2.5), 7.44 (1H, d, J=9.5), 7.49 (1H, d, J=2.0), 7.92 (1H, d, J=2.0), 11.84 (1H, s)

(3) 3-(5-Benzo[b]furanyl)-2'-(6-O-diphenylphosphono-β-D-glucopyranosyloxy)-6'-hydroxy-4'-methylpropiophenone (764 mg) is dissolved in 1,4-dioxane (33 ml), and thereto is added 0.1N aqueous sodium hydroxide solution (33 ml). The mixture is stirred at room temperature for 2.5 hours under argon atmosphere. To the reaction mixture is added ammonium chloride (60 mg), and the mixture is concentrated under reduced pressure. To the residue is added ethanol, and the insoluble materials are removed by filtration. To the filtrate is added isopropanol, and the precipitates are collected by filtration, and dried to give 3-(5-benzo[b]furanyl)-2'-(4,6-O-phosphinico-β-D-glucopyranosyloxy)-6'-hydroxy-4'-methylpropiophenone sodium (327 mg).

ESI-MS (m/z): 519 [(M+Na)$^+$]

IR (nujol, cm-l): 3300,1625, 1612

NMR (DMSO-d$_6$) δ: 2.25 (3H, s), 2.97 (2H, t, J=7.5), 3.3–3.9 (8H, m), 5.15 (1H, d, J=7.5), 5.40 (1H, br), 5.55 (1H, br), 6.41 (1H, s), 6.55 (1H, s), 6.98 (1H, dd, J=1.0, 2.0), 7.19 (1H, dd, J=1.5, 8.5),7.49 (1H, d, J=8.5), 7.51 (1H, d, J=1.5),7.92 (1H, d, J=2.0)

Reference Example 1

(1) Orcinol monohydrate (50 g) is dissolved in pyridine (400 ml), and thereto is added acetic anhydride (133 ml), and the mixture is stirred at room temperature for 17 hours. The reaction mixture is concentrated under reduced pressure, and the resulting residue is dissolved in ethyl acetate (500 ml). The mixture is washed successively with 10% hydrochloric acid, water, a saturated aqueous sodium hydrogen carbonate solution, and a saturated aqueous sodium chloride solution, dried, and concentrated under reduced pressure to give orcinol diacetate (74 g).

EI-MS (m/z): 208 (M$^+$)

NMR (CDCl$_3$) δ:2.27 (6H, s), 2.35 (3H, s), 6.71 (1H, t, J=1.8), 6.80 (2H, m)

(2) Aluminum chloride (19.2 g) is heated at 90° C. in chlorobenzene (50 ml), and thereto is added dropwise a solution of orcinol diacetate (10 g) in chlorobenzene (8 ml) over a period of 35 minutes. After addition, the mixture is stirred at the same temperature for one hour, and cooled. The reaction mixture is poured into ice-10% hydrochloric acid (100 ml—100 ml), and the mixture is stirred for 30 minutes, and extracted with ethyl acetate (100 ml). The organic layer is washed with water, dried, and concentrated under reduced pressure. Hexane (100 ml) is added to the residue, and the mixture is stirred at room temperature for 30 minutes. The precipitates are collected by filtration, and dried to give 2',6'-dihydroxy-4'-methylacetophenone (5.9 g), m.p. 146–148° C.

Reference Example 2

A mixture of 2',6'-dihydroxy-4'-methylacetophenone (0.5 g), cadmium carbonate (2.08 g) and toluene (40 ml) is refluxed while the solvent is removed by a Dean-Stark trap. After 10 ml of the solvent is removed, the mixture is cooled to about 80° C., and thereto is added 2,3,4,6-tetra-O-acetyl-α-D-glucopyranosyl bromide (2.48 g), and the mixture is refluxed overnight. After cooling, the mixture is diluted with chloroform, and the insoluble materials are removed by filtration. The filtrate is concentrated, and the residue is crystallized from methanol to give 2'-(2,3,4,6-tetra-O-acetyl-β-D-glucopyranosyloxy)-6'-hydroxy-4'-methylacetophenone (735 mg).

M.p. 140–141.5° C.

ESI-MS (m/z): 514 [(M+NH$_4$)$^+$]

IR (nujol, cm$^{-1}$): 1755, 1725, 1650

NMR (DMSO-d$_6$) δ: 1.96 (3H, s), 2.01 (9H, s), 2.26 (3H, s), 2.39 (3H, s), 4.05–4.22 (2H, m), 4.28 (1H, ddd, J=2.6, 5.7, 9.9), 5.00 (1H, dd, J=9.5, 9.9), 5.10 (1H, dd, J=8.0, 9.6), 5.39 (1H, t, J=9.5), 5.64 (1H, d, J=8.1), 6.46 (1H, s), 6.48 (1H, s), 11.60 (1H, s)

Reference Example 3

Potassium carbonate (414 g) is suspended in chloroform (1.3 l), and thereto is added dropwise water (29 ml) gradually. To the mixture are added tributylbenzylammonium chloride (37 g), 2',6'-dihydroxy-4'-methylacetophenone (100 g), and 2,3,4,6-tetra-O-acetyl-α-D-glucopyranosyl bromide (419 g), and the mixture is stirred at room temperature for 27 hours. To the mixture is added water (21 ml), and the mixture is stirred for further 2.5 hours. The mixture is neutralized with 18% hydrochloric acid (about 500 ml) under ice-cooling. To the mixture are added 18% hydrochloric acid (about 200 ml) and water (500 ml), and the chloroform layer is separated, washed with water and a saturated aqueous sodium chloride solution, dried, and concentrated. To the residue is added methanol (400 ml), and the mixture is concentrated under reduced pressure to about a half volume thereof. To the resultant is added methanol (2 l), and the mixture is heated a little, and stirred under ice-cooling for 30 minutes. The precipitates are collected by filtration, and dried under reduced pressure to give 2'-(2,3,4,6-tetra-O-acetyl-β-D-glucopyranosyloxy)-6'-hydroxy-4'-methylacetophenone (239.75 g). The physicochemical properties of the compound are the same as those of the compound obtained in Reference Example 2.

Reference Example 4

(1) 3,5-Dimethoxyaniline (1.0 g) is suspended in a mixture of hydrochloric acid (3 ml), acetic acid (2 ml) and water (5 ml), and thereto is added dropwise a solution of sodium nitrite (473 mg) in water (5 ml) under ice-cooling over a period of 15 minutes. Ten minutes thereafter, to the mixture is added a solution of potassium iodide (1.62 g) in water (5 ml), and the mixture is warmed to 80° C., and stirred for one hour. The reaction mixture is extracted with diethyl ether, and the extract is washed with water, dried, and concentrated under reduced pressure. The residue is purified by silica gel column chromatography (solvent; hexane/ethyl acetate), and is recrystallized from ethyl acetate/hexane to give 3,5-dimethoxyiodobenzene (1.05 g), m.p. 73–74° C.

(2) 3,5-Dimethoxyiodobenzene (1.19 g) is dissolved in acetic acid (10 ml), and thereto is added 47% hydrobromic acid (10 ml) at room temperature, and the mixture is refluxed for 15 hours. The reaction mixture is cooled to room temperature, and concentrated to dryness under reduced pressure. The residue is dissolved in ethyl acetate, and the organic layer is washed with water, dried, and concentrated under reduced pressure to give 3,5-dihydroxyiodobenzene (1.06 g).

EI-MS (m/z): 236 (M$^+$)

IR (neat, cm$^{-1}$): 3325, 1605

NMR (CDCl$_3$) δ: 5.22 (2H, s), 6.31 (1H, t, J=2.5), 6.79 (2H, d, J=2.5) (3) 3,5-Dihydroxyiodobenzene (1.02 g) is dissolved in pyridine (2.8 ml), and thereto is added acetic anhydride (1.53 g) at room temperature. The mixture is stirred for one hour, and the reaction mixture is poured into 10% aqueous citric acid solution, and extracted with ethyl acetate. The organic layer is washed with water, dried, and concentrated under reduced pressure to give 3,5-diacetoxyiodobenzene (1.37 g).

EI-MS (m/z): 320 (M$^+$), 278, 236

IR (neat, cm$^{-1}$): 1771, 1586

NMR (CDCl$_3$) δ:2.28 (6H, s), 6.92 (1H, t, J=2.0), 7.36 (2H, d, J=2.0)

(4) 3,5-Diacetoxyiodebonzene (860 mg) is dissolved in 1,4-dioxane (4 ml), and thereto are added vinyl tributyl tin (1.41 g) and dichlorobis(triphenylphosphine)palladium (II) (20 mg) at room temperature. The mixture is refluxed for 3 hours, and cooled to room temperature. The mixture is diluted with ethyl acetate, and thereto is added 10% aqueous potassium fluoride solution. The mixture is stirred at room temperature for 30 minutes, and the insoluble materials arc removed by filtration. The filtrate is extracted with ethyl acetate, and the organic layer is washed with water, dried, and concentrated under reduced pressure. The resulting residue is purified by silica gel column chromatography to give 3,5-diacetoxystyrene (585 mg).

EI-MS (m/z): 220 (M$^+$), 178, 136

IR (neat, cm$^{-1}$): 1771, 1610

NMR (CDCl$_3$) δ: 2.29 (6H, s), 5.32 (1H, d, J=11.0), 5.74 (1H, d, J=17.0), 6.65 (1H, dd, J=11.0, 17.0), 6.82 (1H, t, J=2.0), 7.03 (2H, d, J=2.0)

(5) 3,5-Diacetoxystyrene (580 mg) is dissolved in a mixture of ethyl acetate (6 ml) and ethanol (2 ml), and the mixture is subjected to catalytic reduction with using 10% palladium-carbon (51.4% aqueous, 50 mg) under atmospheric pressure. Two hours thereafter, the catalyst is removed by filtration, and the filtrate is concentrated under reduced pressure. The residue is purified by silica gel column chromatography (solvent; hexane/ethyl acetate) to give 1,3-diacetoxy-5-ethylbenzene (450 mg).

EI-MS (m/z): 222 (M$^+$)

IR (neat, cm$^{-1}$): 1771, 1616

NMR (CDCl$_3$) δ: 1.23 (3H, t, J=7.5), 2.28 (6H, s), 2.66 (2H, q, J=7.5), 6.74 (1H, t, J=2.0), 6.82 (2H, d, J=2.0)

(6) 1,3-Diacetoxy-5-ethylbenzene is treated in the same manner as in Reference Example 1-(2) to give 2',6'-dihydroxy-4'-ethylacetophenone, m.p. 121–123° C.

(7) 2',6'-Dihydroxy-4'-ethylacetophenone is treated in the same manner as in Reference Example 3 to give 2'-(2,3,4,6-tetra-O-acetyl-β-D-glucopyranosyloxy)-6'-hydroxy-4'-ethylacetophenone, m.p. 125–127° C.

Reference Example 5

(1) Zinc powder (purity; 85%, 14.75 g) is suspended in N,N-dimethylformamide (50 ml) under argon atmosphere, and thereto is added dropwise with stirring acetyl chloride (1.06 g) at 50° C. over a period of 10 minutes, and then the mixture is stirred for 15 minutes. To the mixture is added dropwise a solution of 3,5-dimethoxybenzaldehyde (10 g) in dibromomethane (15.69 g) over a period of 20 minutes, and the mixture is stirred for 30 minutes. The reaction solution is cooled with ice, and thereto is added dropwise a saturated aqueous ammonium chloride solution (40 ml), and further thereto is added diethyl ether. The insoluble materials are removed by filtration, and the filtrate is extracted with diethyl ether. The extract is washed successively with 10% hydrochloric acid, water, 10% aqueous sodium hydroxide solution, and a saturated aqueous sodium chloride solution, dried, and concentrated under reduced pressure to give 3,5-dimethoxystyrene (8.29 g).

EI-MS (m/z): 164 (M$^+$), 149, 135, 121

IR (neat, cm$^{-1}$): 1620, 1595

NMR (CDCl$_3$) δ: 3.80 (6H, s), 5.25 (1H, dd, J=1.0, 11.0), 5.72 (1H, dd, J=1.0, 17.5), 6.39 (1H, t, J=2.5), 6.57 (2H, d, J=2.5), 6.64 (1H, dd, J=11.0, 17.5)

(2) 3,5-Dimethoxystyrene (8.29 g) is dissolved in a mixture of methanol (70 ml) and ethyl acetate (10 ml), and the mixture is subjected to catalytic hydrogenation with using 10% palladium-carbon (51.4% aqueous, 1.2 g) under atmospheric pressure. One hour thereafter, the catalyst is removed by filtration, and the filtrate is concentrated under reduced pressure. The residue is purified by silica gel column chromatography (solvent; hexane/ethyl acetate) to give 1,3-dimethoxy-5-ethylbenzene (7.07 g).

EI-MS (m/z): 166 (M$^+$), 151, 137

IR (neat, cm$^{-1}$): 1607, 1596

NMR (CDCl$_3$) δ: 1.22 (3H, t, J=7.5), 2.60 (2H, q, J=7.5), 3.78 (6H, s), 6.30 (1H, t, J=2.5), 6.37 (2H, d, J=2.5)

(3) 1,3-Dimethoxy-5-ethylbenzene (7.69 g) is dissolved in acetic acid (80 ml), and thereto is added with stirring 47% hydrobromic acid at room temperature. The mixture is refluxed for three hours, and the reaction mixture is cooled to room temperature. The mixture is concentrated to dryness under reduced pressure, and the residue is dissolved in ethyl acetate. The organic layer is washed successively with water and a saturated aqueous sodium chloride solution, dried, and concentrated under reduced pressure. The residue is recrystallized from diisopropyl ether-hexane to give 1,3-dihydroxy-5-ethylbenzene (5.94 g), m.p. 97–98° C.

(4) 1,3-Dihydroxy-5-ethylbenzene (5.92 g) is dissolved in pyridine (32 ml), and thereto is added with stirring acetic anhydride (17.5 g) at room temperature. One hour thereafter, the reaction mixture is poured into chilled 10% hydrochloric acid, and the mixture is extracted with ethyl acetate. The organic layer is washed successively with water, a saturated aqueous sodium hydrogen carbonate solution, and a saturated aqueous sodium chloride solution, dried, and concentrated under reduced pressure to give 1,3-diacetoxy-5-ethylbenzene (9.60 g). The physicochemical properties are the same as those of the compound obtained in Reference Example 4-(5).

EFFECTS OF THE INVENTION

The compounds (I) of the present invention and a pharmaceutically acceptable salts thereof show an excellent hypoglycemic activity because of the increasing effect of the urine glucose excretion, based on the inhibition activity of renal tubular glucose reabsorption. For example, when administered orally to rats, the present compounds increase the amount of urine glucose more than 50 times as much as phlorizin does.

In addition, the compounds (I) of the present invention show low toxicity. Besides, the aglycone of the compounds (I), the hydrolysate thereof, show extremely a weak inhibitory activity against facilitated diffusion-type glucose transporter.

Therefore, the compounds (I) of the present invention can treat hyperglycemia, by which the self-exacerbating cycle of glucose toxicity is interrupted, so that the compounds (I) are useful in the prophylaxis or treatment of diabetes [e.g., diabetes mellitus such as insulin-dependent diabetes(type I diabetes), insulin-independent diabetes (type II diabetes)], or in the rectification of hyperglycemia after meal.

What is claimed is:

1. A propiophenone derivative of the formula (I):

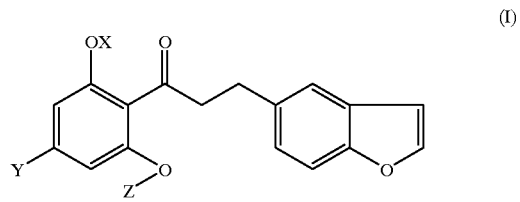

wherein OX is a hydroxy group which may optionally be protected, Y is a lower alkyl group, and Z is a β-D-glucopyranosyl group wherein one or more hydroxy groups may optionally be protected, or a pharmaceutically acceptable salt thereof.

2. The compound according to claim 1, wherein Z is (i) a β-D-glucopyranosyl group wherein one or more hydroxy groups may optionally be acylated, (ii) a β-D-glucopyranosyl group wherein two hydroxy groups combine to form a 1-lower alkoxy-lower alkylidenedioxy group, a benzylidenedioxy group, a phosphinicodioxy group, or a carbonyldioxy group together with the protecting groups thereof, or (iii) a β-D-glucopyranosyl group wherein one or two hydroxy groups are acylated, and two hydroxy groups combine to form a 1-lower alkoxy-lower alkylidenedioxy group, a benzylidenedioxy group, a phosphinicodioxy group, or a carbonyldioxy group together with the protecting groups thereof.

3. The compound according to claim 2, wherein Z is a β-D-glucopyranosyl group wherein one or more hydroxy groups may optionally be acylated by a group selected from the group consisting of a lower alkanoyl group, a lower alkoxycarbonyl group, a lower alkoxy-lower alkanoyl group and a lower alkoxy-lower alkoxycarbonyl group, or a β-D-glucopyranosyl group wherein two hydroxy groups combine form a 1-lower alkoxy-lower alkylidenedioxy group or a phosphinicodioxy group together with the protecting groups thereof.

4. The compound according to claim 3, wherein Z is a β-D-glucopyranosyl group wherein the 2-hydroxy group, or the 2- and the 3-hydroxy groups, or the 4-hydroxy group, or the 6-hydroxy group may optionally be acylated by a group selected from the group consisting of a lower alkanoyl group, a lower alkoxycarbonyl group, a lower alkoxy-lower alkanoyl group and a lower alkoxy-lower alkoxycarbonyl group, or a β-D-glucopyranosyl group wherein 4- and 6-hydroxy groups combine to form a 1-lower alkoxy-lower alkylidenedioxy group or a phosphinicodioxy group together with the protecting groups thereof.

5. The compound according to claim 4, wherein OX is a hydroxy group, a lower alkanoyloxy group, or a lower alkoxycarbonyloxy group, and Z is a β-D-glucopyranosyl group, a 2-O-(lower alkanoyl)-β-D-glucopyranosyl group, a 2,3-di-O-(lower alkanoyl)-β-D-glucopyranosyl group, a 4-O-(lower alkoxycarbonyl)-β-D-glucopyranosyl group, a 6-O-(lower alkanoyl)-β-D-glucopyranosyl group, a 6-O-(lower alkoxycarbonyl)-β-D-glucopyranosyl group, a 6-O-(lower alkoxy-lower alkanoyl)-β-D-glucopyranosyl group, a 6-O-(lower alkoxy-lower alkoxycarbonyl)-β-D-glucopyranosyl group, a 4,6-O-(1-lower alkoxy-lower alkylidene)-β-D-glucopyranosyl group, or a 4,6-O-phosphinico-β-D-glucopyranosyl group.

6. The compound according to claim 5, wherein OX is a hydroxy group or a lower alkanoyloxy group, and Z is a β-D-glucopyranosyl group, a 2,3-di-O-(lower alkanoyl)-β-D-glucopyranosyl group, a 4-O-(lower alkoxycarbonyl)-β-D-glucopyranosyl group, a 6-O-lower alkoxycarbonyl)-β-D-glucopyranosyl group, a 4,6-O-(1-lower alkoxy-lower alkylidene)-β-D-glucopyranosyl group, or a 4,6-O-phosphinico-β-D-glucopyranosyl group.

7. The compound according to claim 6, wherein OX is a hydroxy group, Y is a methyl group or an ethyl group, and Z is a β-D-glucopyranosyl group, a 4-O-(lower alkoxycarbonyl)-β-D-glucopyranosyl group, a 6-O-(lower alkoxy-carbonyl)-β-D-glucopyranosyl group, a 4,6-O-(1-lower alkoxy-lower alkylidene)-β-D-glucopyranosyl group, or a 4,6-O-phosphinico-β-D-glucopyranosyl group.

8. The compound according to claim 7, wherein Z is a β-D-glucopyranosyl group or a 6-O-(lower alkoxycarbonyl)-β-D-glucopyranosyl group.

9. 3-(5-Benzo[b]furanyl)-2'-(β-D-glucopyranosyloxy)-6'-hydroxy-4'-methylpropiophenone or a pharmaceutically acceptable salt thereof.

10. 3-(5-Benzo[b]furanyl)-2'-(6-O-methoxycarbonyl-β-D-glucopyranosyloxy)-6'-hydroxy-4'-methylpropiophenone or a pharmaceutically acceptable salt thereof.

11. A process for preparing a propiophenone derivative of the formula (I):

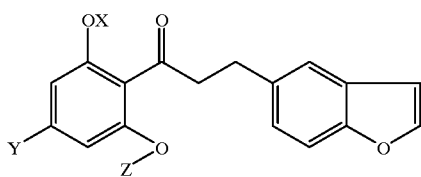

(I)

wherein OX is a hydroxy group which may optionally be protected, Y is a lower alkyl group, and Z is a β-D-glucopyranosyl group wherein one or more hydroxy groups may optionally be protected, or a pharmaceutically acceptable salt thereof, which comprises reducing a compound of the formula (II):

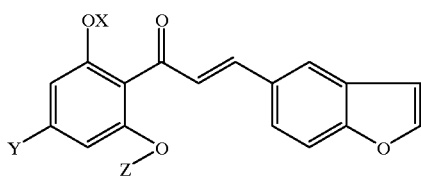

(II)

wherein OX, Y and Z are the same as defined above, and if necessary, followed by converting the product into a pharmaceutically acceptable salt thereof.

12. A process for preparing a propiophenone derivative of the formula (I-b):

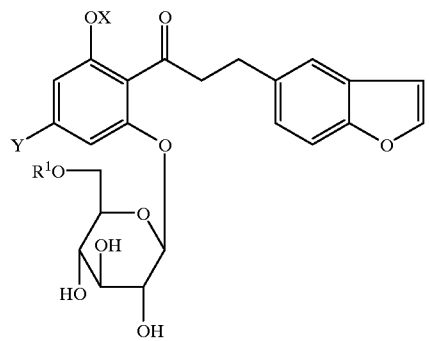

(I-b)

wherein $R^1$ is an acyl group, OX is a hydroxy group which may optionally be protected, and Y is a lower alkyl group, or a pharmaceutically acceptable salt thereof, which comprises acylating a compound of the formula (I-a):

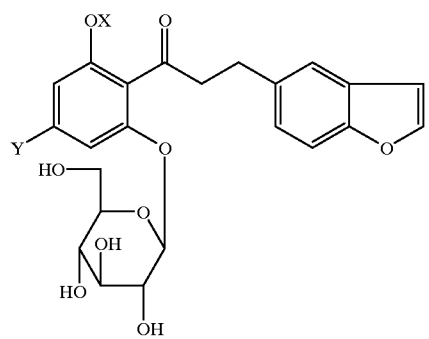

(I-a)

wherein OX and Y are the same as defined above, and if necessary, followed by converting the product into a pharmaceutically acceptable salt thereof.

13. A process for preparing a propiophenone derivative of the formula (I-c):

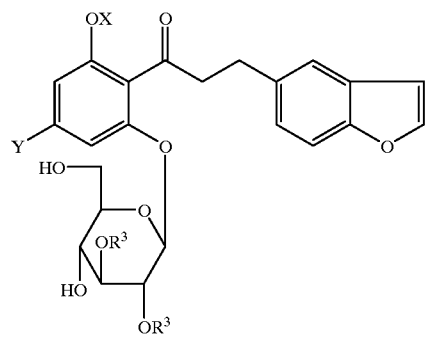

(I-c)

wherein $R^3$ is an acyl group, OX is a hydroxy group which may optionally be protected, and Y is a lower alkyl group, or a pharmaceutically acceptable salt thereof, which comprises acylating a compound of the formula (I-d):

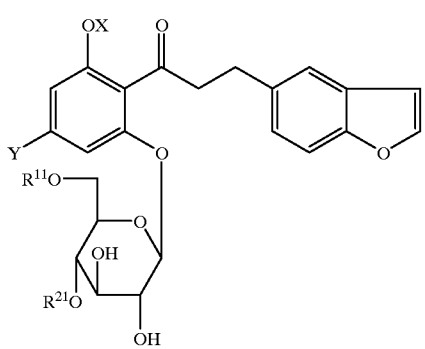

(I-d)

wherein R¹¹O and R²¹O are protected hydroxy groups, and OX and Y are the same as defined above, removing the protecting groups from the product, and if necessary, followed by converting the product into a pharmaceutically acceptable salt thereof.

14. A process for preparing a propiophenone derivative of the formula (I-e):

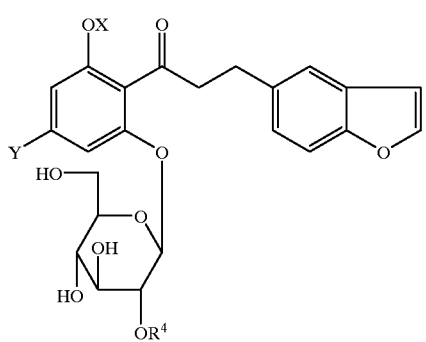

(I-e)

wherein $R^4$ is an acyl group, OX is a hydroxy group which may optionally be protected, and Y is a lower alkyl group, or a pharmaceutically acceptable salt thereof, which comprises acylating a compound of the formula (I-f):

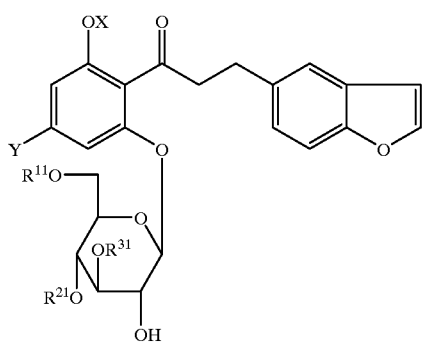

(I-f)

wherein R¹¹O, R²¹O and R³¹O are protected hydroxy groups, and OX and Y are the same as defined above, removing the protecting groups from the product, and if necessary, followed by converting the product into a pharmaceutically acceptable salt thereof.

15. A process for preparing a propiophenone derivative of the formula (I-g):

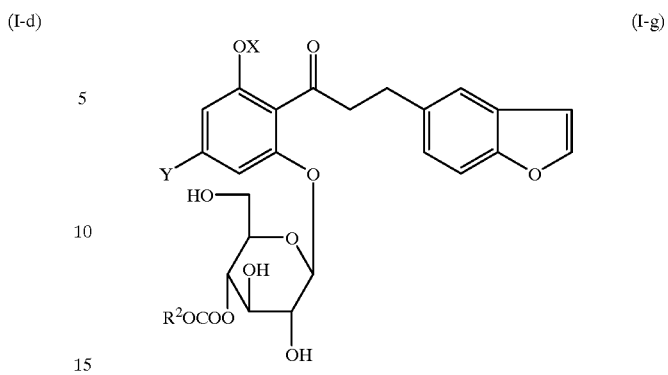

(I-g)

wherein $R^2$ is a lower alkyl group, OX is a hydroxy group which may optionally be protected, and Y is a lower alkyl group, or a pharmaceutically acceptable salt thereof, which comprises reacting a compound of the formula (I-h):

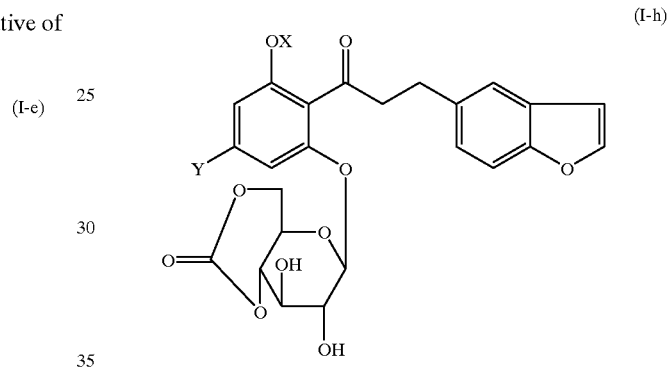

(I-h)

wherein OX and Y are the same as defined above, with a compound of the formula (III):

$$R^2OH \quad \text{(III)}$$

wherein $R^2$ is the same as defined above, and if necessary, followed by converting the product into a pharmaceutically acceptable salt thereof.

16. A process for preparing a propiophenone derivative of the formula (I-i):

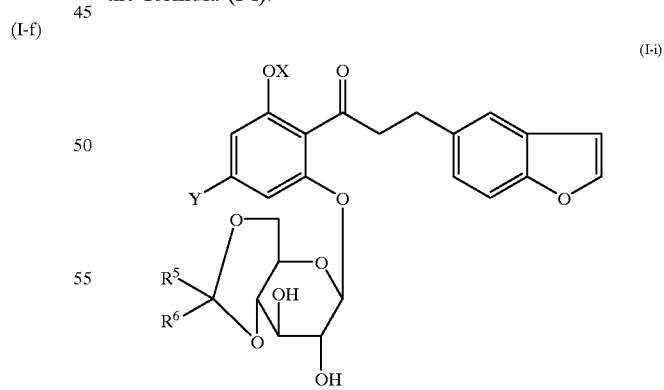

(I-i)

wherein $R^5$ is a hydrogen atom or a lower alkyl group and $R^6$ is a lower alkoxy group, or $R^5$ is a hydrogen atom and $R^6$ is a phenyl group, $R^5$ and $R^6$ may combine to form an oxo group, OX is a hydroxy group which may optionally be protected, and Y is a lower alkyl group, or a pharmaceutically acceptable salt thereof, which comprises reacting a compound of the formula (I-a):

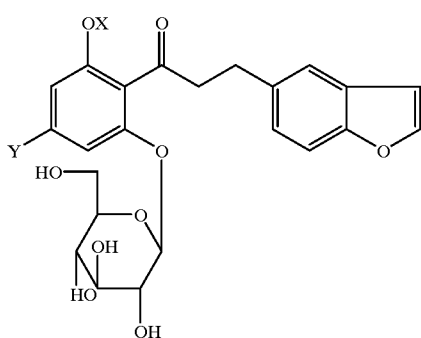
(I-a)

wherein OX and Y are the same as defined above, with a compound of the formula (IV):

(IV)

wherein $A^1$ and $A^2$ are leaving groups, and $R^5$ and $R^6$ are the same as defined above, and if necessary, followed by converting the product into a pharmaceutically acceptable salt thereof.

17. A process for preparing a propiophenone derivative of the formula (I-j):

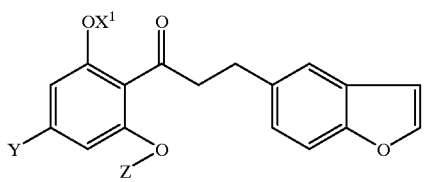
(I-j)

wherein $OX^1$ is a protected hydroxy group, Y is a lower alkyl group, and Z is a β-D-glucopyranosyl group wherein one or more hydroxy groups may optionally be protected, or a pharmaceutically acceptable salt thereof, which comprises protecting the 6'-phenolic hydroxy group of a compound of the formula (I-k):

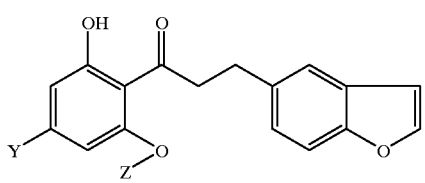
(I-k)

wherein Y and Z are the same as defined above, and if necessary, followed by converting the product into a pharmaceutically acceptable salt thereof.

18. A process for preparing a propiophenone derivative of the formula (I-k):

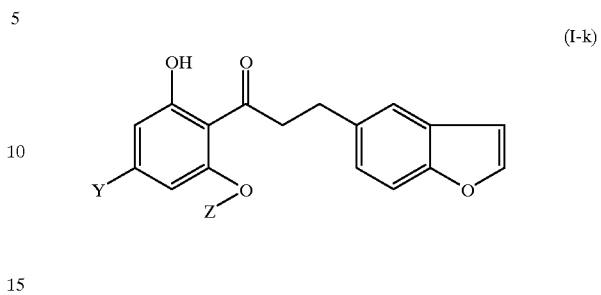
(I-k)

wherein Y is a lower alkyl group, and Z is a β-D-glucopyranosyl group wherein one or more hydroxy groups may optionally be protected, or a pharmaceutically acceptable salt thereof, which comprises removing the protecting group from a compound of the formula (I-j):

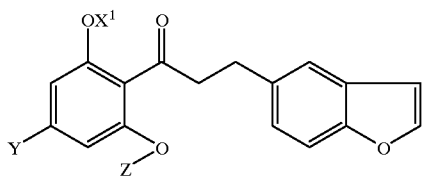
(I-j)

wherein $OX^1$ is a protected hydroxy group, and Y and Z are the same as defined above, and if necessary, followed by converting the product into a pharmaceutically acceptable salt thereof.

19. A process for preparing a compound of the formula (I-l):

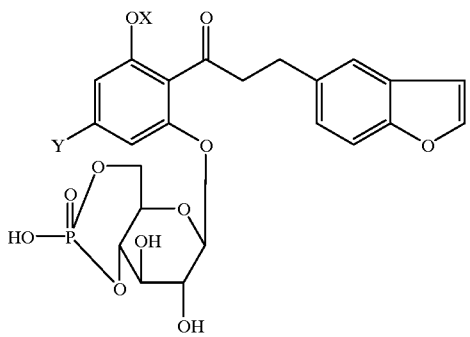
(I-l)

wherein OX is a hydroxy group which may optionally be protected, and Y is a lower alkyl group, or a pharmaceutically acceptable salt thereof, which comprises subjecting a compound of the formula (I-m):

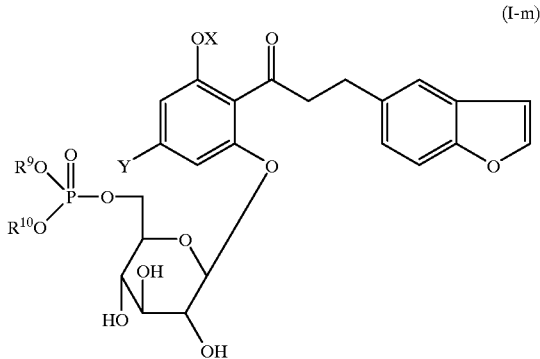

(I-m)

wherein $R^9$ and $R^{10}$ are the same or different and each protecting groups for hydroxy group, and OX and Y are the same as defined above, to hydrolysis, and if necessary, followed by converting the product into a pharmaceutically acceptable salt thereof.

20. A pharmaceutical composition which comprises a therapeutically effective amount of the compound as set forth in claim 1 in admixture with a pharmaceutically acceptable carrier or diluent.

21. A method for prophylaxis or treatment of diabetes in a patient, which comprises administering to said patient a therapeutically effective amount of the compound as set forth in claim 1.

22. A method for increasing the amount of glucose in urine in a patient in need thereof, which comprises administering to said patient a therapeutically effective amount of the compound as set forth in claim 1.

23. A method for lowering blood glucose concentration comprising increasing the amount of glucose in urine with the method of claim 22.

24. A method for treatment of hyperglycemia in a patient, which comprises administering to said patient a therapeutically effective amount of the compound as set forth in claim 1.

* * * * *